United States Patent [19]
Strul et al.

[11] Patent Number: 5,540,681
[45] Date of Patent: Jul. 30, 1996

[54] METHOD AND SYSTEM FOR RADIOFREQUENCY ABLATION OF TISSUE

[75] Inventors: Bruno Strul, Palo Alto; Kevin C. Ladd, Redwood City, both of Calif.

[73] Assignee: Medtronic Cardiorhythm, San Jose, Calif.

[21] Appl. No.: 179,558

[22] Filed: Jan. 10, 1994

Related U.S. Application Data

[63] Continuation-in-part of Ser. No. 866,683, Apr. 10, 1992.
[51] Int. Cl.$^6$ ................................................. A61B 17/36
[52] U.S. Cl. ................................ 606/34; 606/1; 606/42; 606/45; 606/31; 607/101; 607/102
[58] Field of Search ........................... 606/27–35, 37–42; 607/100–102, 154

[56] References Cited

U.S. PATENT DOCUMENTS

| | | |
|---|---|---|
| 1,935,289 | 11/1933 | Evans . |
| 3,588,710 | 6/1971 | Masters . |
| 3,601,126 | 8/1971 | Estes . |
| 3,785,383 | 1/1974 | Dotto . |
| 3,800,802 | 4/1974 | Berry et al. . |
| 4,196,734 | 4/1980 | Harris ........................................ 606/38 |
| 4,204,549 | 5/1980 | Paglione . |
| 4,352,156 | 9/1982 | Gyugyi . |
| 4,494,539 | 1/1985 | Zenitani et al. . |
| 4,580,557 | 4/1986 | Hertzmann ................................ 606/13 |
| 4,590,934 | 5/1986 | Malis et al. ................................ 606/37 |
| 4,599,553 | 7/1986 | Brennen et al. . |
| 4,632,127 | 12/1986 | Sterzer . |
| 4,658,819 | 4/1987 | Harris et al. . |
| 4,692,685 | 9/1987 | Blaze . |
| 4,716,897 | 1/1988 | Noguchi et al. . |
| 4,727,874 | 3/1988 | Bowers et al. . |
| 4,739,759 | 4/1988 | Rexroth et al. . |
| 4,805,621 | 2/1989 | Heinze et al. . |
| 4,860,744 | 8/1989 | Johnson et al. ........................... 606/29 |
| 4,862,889 | 9/1989 | Feucht . |
| 4,878,493 | 11/1989 | Pasternak et al. . |
| 4,907,589 | 3/1990 | Cosman ..................................... 606/41 |
| 4,945,912 | 8/1990 | Langberg . |
| 4,960,134 | 10/1990 | Webster, Jr. . |
| 4,966,597 | 10/1990 | Cosman . |
| 5,057,105 | 10/1991 | Malone et al. ........................... 606/28 |
| 5,122,137 | 6/1992 | Lennox .................................... 606/42 |
| 5,167,660 | 12/1992 | Altendorf ................................. 606/40 |
| 5,318,563 | 6/1994 | Malis et al. .............................. 606/34 |
| 5,383,874 | 1/1995 | Jackson et al. ........................... 606/1 |

FOREIGN PATENT DOCUMENTS

| | | |
|---|---|---|
| 0136855 | 4/1985 | European Pat. Off. . |
| 0368532 | 5/1990 | European Pat. Off. . |
| 2164473 | 3/1986 | United Kingdom . |
| WO91/03208 | 3/1991 | WIPO . |
| WO91/16859 | 11/1991 | WIPO . |
| WO93/08756 | 5/1993 | WIPO . |
| WO93/08757 | 5/1993 | WIPO . |

Primary Examiner—Stephen C. Pellegrino
Assistant Examiner—Michael Peffley
Attorney, Agent, or Firm—Townsend and Townsend and Crew

[57] ABSTRACT

A system for delivering radiofrequency energy to ablate tissue comprises a radiofrequency generator and an intravascular catheter. The catheter includes both a radiofrequency ablation electrode and a temperature sensor within its distal end. Delivery of power to the ablation electrode may then be controlled based on electrode temperature using a cascade control system wherein analog temperature controller adjusts the set point to a secondary power controller. Alternatively, power delivered to the patient can be controlled directly based on a power set point. A sinusoidal RF signal is provided to avoid energy attenuation and the sinusoidal RF signal may be pulsed to avoid buildup of coagulum on the catheter tip while providing high power to create large lesions. A verification circuit checks the continuity of circuits in the catheter.

17 Claims, 31 Drawing Sheets

| FIG. 7A. | FIG. 7B. | FIG. 7C. |
| --- | --- | --- |
| FIG. 7D. | FIG. 7E. | FIG. 7F. |

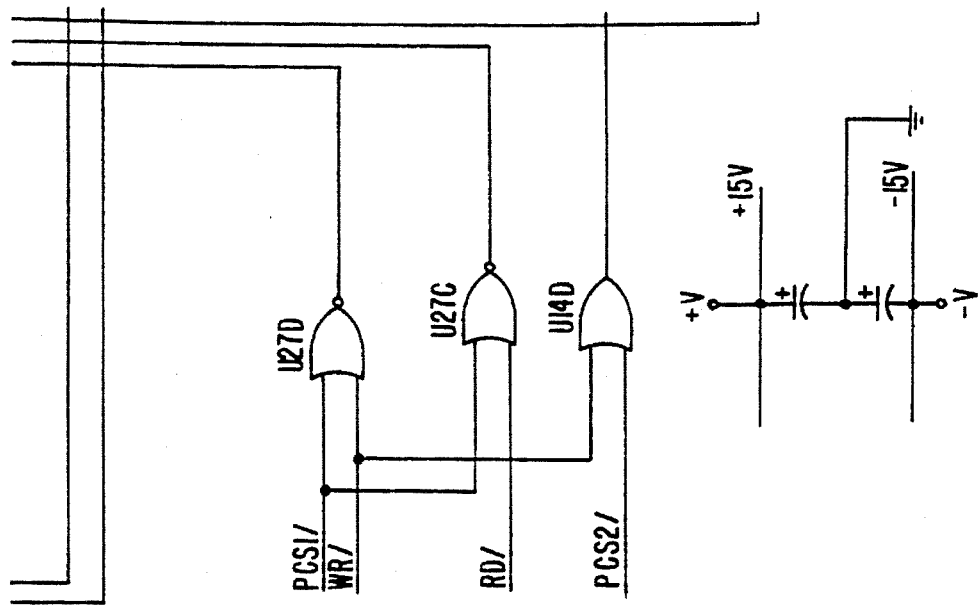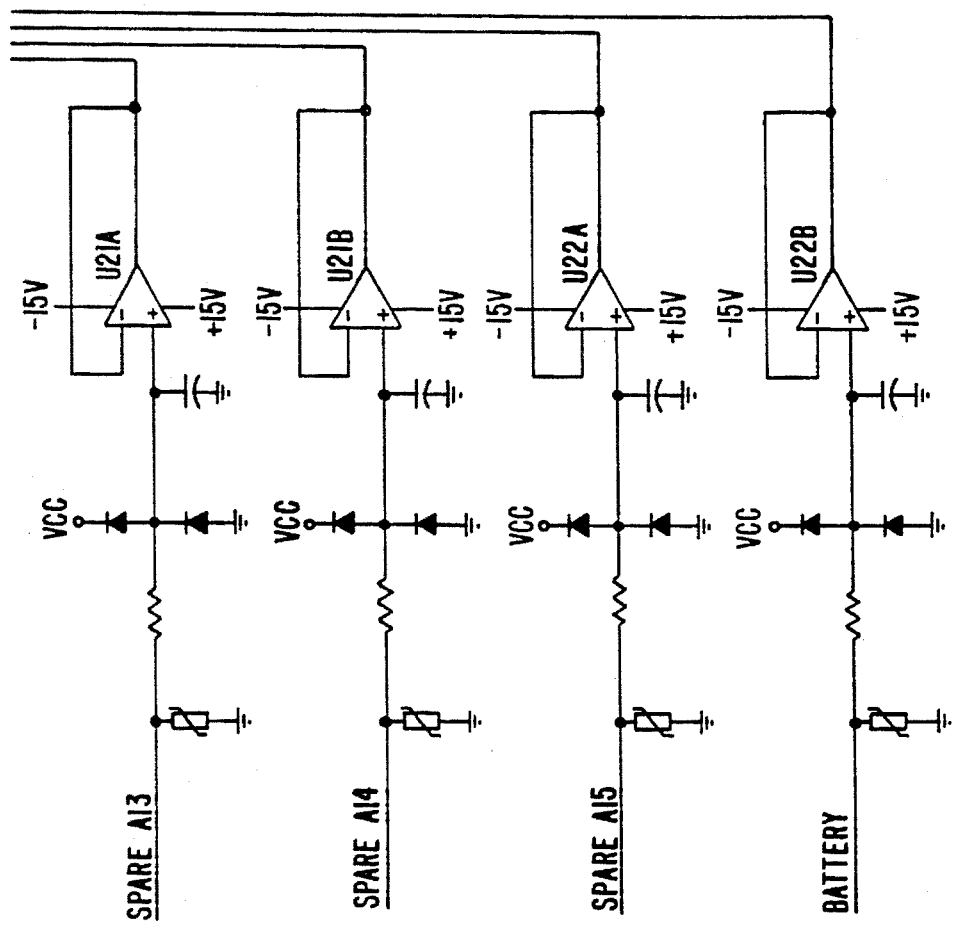
FIG. 9C.
FIG. 9.

METHOD AND SYSTEM FOR RADIOFREQUENCY ABLATION OF TISSUE

This application is a Continuation-in-Part of U.S. Ser. No. 07/866,683, filed Apr. 10, 1992.

BACKGROUND OF THE INVENTION

1. Field of the Invention

The present invention relates generally to the field of electrophysiology. More particularly, this invention relates to methods and apparatus for treating cardiac arrhythmias.

Symptoms of abnormal heart rhythm are generally referred to as cardiac arrhythmias, with an abnormally slow rhythm being classified as a bradycardia and an abnormally rapid rhythm being referred to a tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for the normal electrical function. The presence of arrhythmogenic sites or accessory pathways can bypass or short circuit the normal pathways, potentially resulting in very rapid heart contractions, referred to as tachycardias. Tachycardias may be defined as ventricular tachycardias (VTs) and supraventricular tachycardias (SVTs). VTs originate in the left or right ventricle and are typically caused by arrhythmogenic sites associated with a prior myocardial infarction. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention are radiofrequency ablation protocols which have proven to be highly effective in tachycardia treatment while exposing the patient to minimum side effects and risks.

Radiofrequency catheter ablation is generally performed after an initial mapping procedure where the location of the arrhythmogenic sites and accessory pathways are determined. After mapping, a catheter having a suitable electrode is introduced to the appropriate chamber and manipulated so that the electrode lies proximate the accessory pathway. Radiofrequency energy is then applied through the electrode to the cardiac tissue in order to ablate a region of the tissue which forms part of the accessory pathway. By successfully destroying that tissue, the accessory pathway or arrhythmogenic site is destroyed so that the abnormal signalling patterns responsible for the tachycardia will no longer occur.

While very promising, radiofrequency ablation suffers from certain disadvantages. The application of radiofrequency energy to the heart tissue can have complications, particularly if the directed energy has not been properly controlled. Many systems which have been used thus far for radiofrequency ablation have utilized radiofrequency power supplies originally intended for electrosurgery and electrocautery. While such power supplies are workable, they do not provide power control of a type which is best used with cardiac tissue ablation and can subject the patient to spurious ground potentials. Such ground potentials can be a problem when the heart is being treated. Such conventional radiofrequency power supplies are also usually bulky and relatively heavy because of the need to provide power supply transformers.

2. Description of the Background Art

The successful treatment of supraventricular and ventricular tachycardias by radiofrequency catheter ablation of accessory atrioventricular pathways is described in Kuck et al. (1991) Lancet 337:1557–61; Langberg et al. (1991) Am. J. Cardiol. 67:142–47; and Kuck et al. (1991) Circulation 84:2366–2375. Catheters useful for the intracardiac application of radiofrequency energy are described in U.S. Pat. Nos. 4,945,912; 4,940,064; and 4,641,649. A power supply and radiofrequency ablation catheter suitable for intracardiac tissue ablation are available from Dr. Osypka GMBH under the tradenames HAT 200 S and CERABLATE®, respectively. The power supply and catheter together permit ablation to be performed under a digital temperature control mode. The present state of cardiac radiofrequency ablation treatment is summarized in Fackelmann (1991) Science News 140:42–43.

SUMMARY OF THE INVENTION

An improved method for radiofrequency ablation of cardiac tissue relies on the introduction of an electrode to a target site, typically the location of an accessory pathway, within an interior chamber of a patient's heart. Radiofrequency energy is applied to the target location through the electrode from an external power source, where the amount of radiofrequency energy delivered is controlled based on a particular temperature control protocol which has been found to provide very precise control of the ablation temperature. Such precise temperature control reduces the risk of unintended damage to the cardiac tissue and, in particular, provides for better localization of the treatment. That is, tissue necrosis is more accurately limited to within the target region than with non-temperature controlled protocols. The temperature control protocol also limits the total amount of energy delivered to achieve the desired tissue ablation by controlling the magnitude of the radiofrequency signal to be proportional to the difference between the actual temperature of the tissue being ablated and a target temperature. According to another aspect of the invention, a battery power source is advantageously utilized to reduce or eliminate the generation of spurious ground differential currents, which can be a particular problem in equipment used with the heart.

The temperature control protocol comprises measuring temperature at the target location, typically using a temperature sensor within the treatment electrode. The resulting actual temperature signal is amplified and then compared with a temperature set point signal, and a power set point signal is produced based on the deviation between the actual temperature and temperature set point. Power output from the power source (typically an output power oscillator connected to a battery) is measured to produce an actual power signal, and the actual power signal is compared with the power set point to produce a power output signal based on the difference between the set point and the actual power. Power from the power source is then controlled based on the power output signal. Usually, both the temperature control and power control loops will be based on proportional control schemes.

According to another aspect of the invention, for high power applications a sinusoidal RF signal is generated and modulated by a power output signal. Unlike a square wave RF signal, the sinusoidal signal does not need to be filtered to remove interference so attenuation of power is avoided.

According to a further aspect of the invention, an RF power signal generator provides a series of digital signals representing a sinusoidal function. These signal are converted to an analog sinusoidal signal by a multiplying DAC. The power output signal is provided to a reference voltage input of the DAC and the amplitude of the analog sinusoidal signal is varied according to the amplitude of the power output signal.

According to a still further aspect of the invention, the temperature modulated RF signal is pulsed to prevent the formation of coagulum on the tip due to increasing tip temperature. This pulsing allows the tip to cool because of its high thermal conductivity while transferring high energy to the tissue to cause the formation of deep lesions.

According to a still further aspect of the invention, a controller alternately provides power enable and disable signals at preselected time intervals. An RF signal generator circuit receives the power enable and disable signals and provides a sinusoidal RF signal only when the power enable signal is received and provides a null signal otherwise.

The present invention further provides a radiofrequency power generator which comprises a power source for producing radiofrequency power based on a power output signal. The generator comprises circuitry for measuring the amount of radiofrequency power produced by the power source to produce an actual power signal. An analog temperature controller receives both a temperature set point and an actual temperature signal and, based on the difference therebetween, produces a power set point signal. A separate analog power controller receives the power set point signal from the temperature controller and the actual power signal from the power measurement circuitry, and, based on the difference therebetween, produces the power output signal which controls the power source. The generator further comprises an interface for connecting a catheter to the radiofrequency power source and for connecting an external temperature sensor in the catheter to the temperature controller in the generator.

According to a still further aspect of the invention, in addition to temperature control, an alternative control signal is provided indicating a selected power level and the radiofrequency power delivered to the electrode is limited according to the selected power level irrespective of the temperature set point. Thus, an additional safety feature is provided for limiting the power from exceeding a selected level.

Other advantages and features of the invention will be apparent to persons skilled in the art in view of the following detailed description and appended drawings.

DESCRIPTION OF THE DRAWINGS

FIGS. 7, 7a–7f, 8, 8a–8d, 9, 9a–9d, 10, 10a–10d, 11, 11a–11c, 12, and 12a–12c are schematic diagrams illustrating the circuitry of the radiofrequency generator of FIG. 4.

DESCRIPTION OF SPECIFIC EMBODIMENTS

The method and apparatus of the present invention are intended for delivering radiofrequency energy to a target location within an interior chamber within a patient's heart, usually the right or left ventricle. The target location will be associated with cardiac tachycardia, usually being an accessory pathway or an arrhythmogenic site responsible for the tachycardia, but also including regions on the bundle of HIS which can non-specifically block tachycardia. Accessory pathways or arrhythmogenic sites responsible for the tachycardia can be identified by conventional intracardiac mapping, as is now amply described in the medical and patent literature. See, for example, U.S. Pat. Nos. 4,699,147; 4,628, 937; and 4,660,571, the disclosures of which are incorporated herein by reference. See also copending application Ser. No. 07/866,763, the disclosure of which is incorporated herein by reference.

Radiofrequency ablation involves the application of radiofrequency energy, typically at a frequency in the range from about 250 to 1000 kHz, usually in the range from about 400 to 500 kHz, at a power level sufficient to raise the target tissue to a sufficiently high temperature for a time sufficient to induce tissue necrosis. Typically, the tissue temperature will be above about 45° C., usually being above about 60° C., but usually not exceeding about 105° C. and preferably being maintained below about 95° C. For such temperatures, the radiofrequency energy will typically be applied for time periods in the range from about 30 to 60 seconds, but time periods as short as 10 seconds and as along as 90 seconds also find use.

In order to deliver the radiofrequency energy to the desired target location within the heart, an intravascular catheter having a suitable electrode near its distal end will be percutaneously introduced, typically through the femoral vein or artery in the patient's groin. The distal tip of the catheter can then be manipulated by conventional means, typically through a previously introduced guiding catheter, until it reaches the interior of the heart. The electrode tip of the catheter will then be further manipulated so that it contacts the desired region within the interior of the heart chamber, typically the location of an accessory pathway, a location on the bundle of HIS, an arrhythmogenic site in the ventricular wall, or the like. Radiofrequency power will then be applied to the target location according to the method of the present invention, as described in more detail hereinafter. Preferably, the radiofrequency power will be applied using a radiofrequency generator and system of the present invention, also as described in more detail hereinafter.

Figure 1:
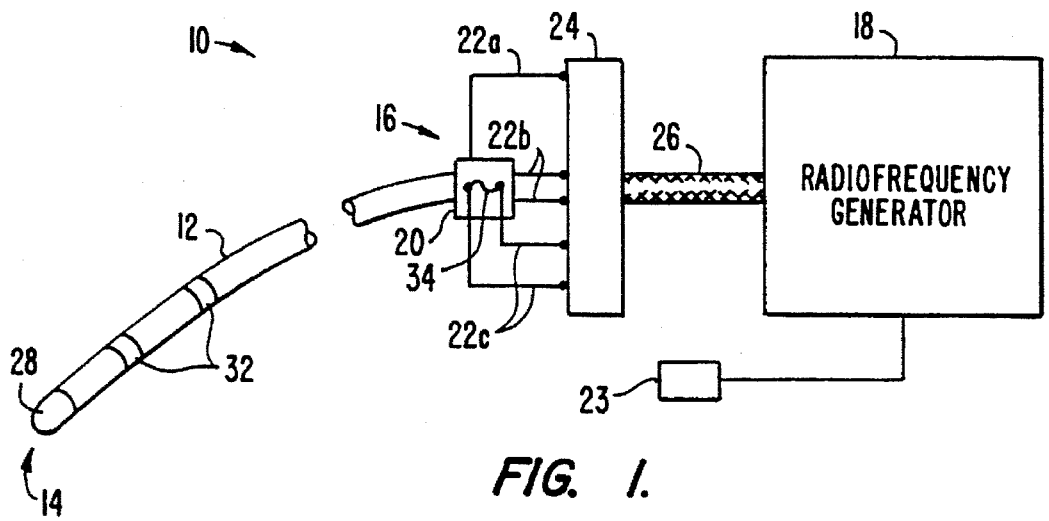
FIG. 1 is a schematic illustration of a system for radiofrequency ablation of cardiac tissue constructed in accordance with the principles of the present invention, comprising a catheter connected to a radiofrequency generator.

Referring now to FIG. 1, an exemplary radiofrequency ablation system 10 constructed in accordance with the principles of the present invention includes a catheter 12 having a distal end 14, a proximal end 16, and a radiofrequency generator 18 connected to the catheter as described below. The proximal end 16 of the catheter 12 includes a proximal housing 20 having a plurality of connecting wires 22 that will normally terminate in a connector 24. The radiofrequency generator 18 is connected to the connector 24 through a cable 26. In this way, all active electrical components (as described hereinafter) of the catheter 12 may be removably connected to the radiofrequency generator 18 simply by plugging the catheter connector 24 into the cable 26.

Figure 2:
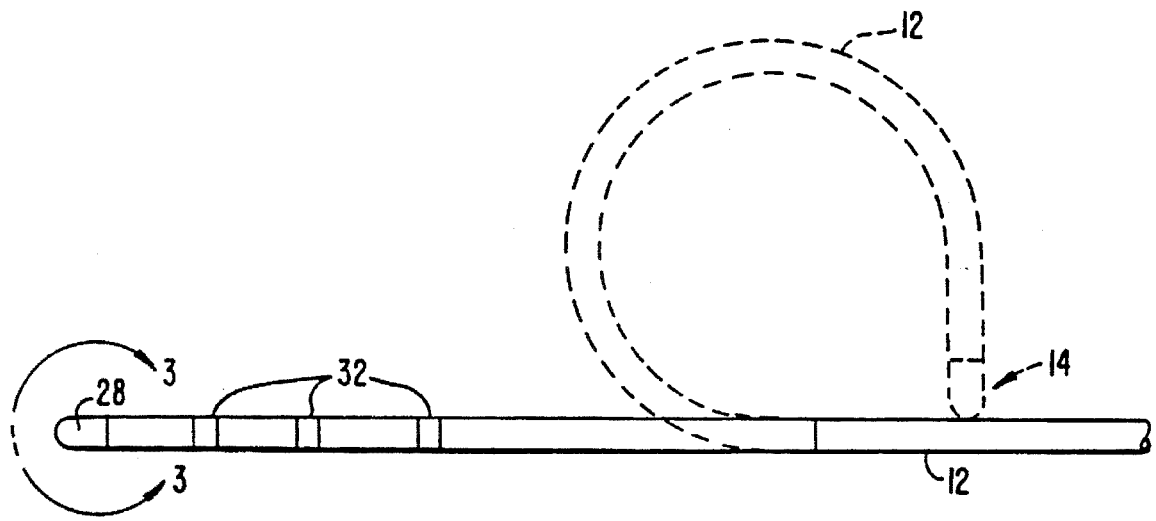
FIG. 2 is an enlarged view of the catheter of FIG. 1, with a curved tip shown in broken line.
Figure 3:
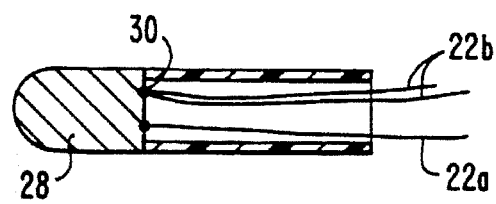
FIG. 3 is a detailed view of the catheter of FIGS. 1 and 2, shown in section.

Referring now to FIGS. 1–3, the catheter 12 includes an electrode 28 near its distal end, usually being at the distal tip, which is connected to a wire 22a which provide a monopolar power connection to the electrode 28 for applying radiofrequency energy from the generator 18, as will be described in greater detail hereinafter. An indifferent electrode 23 is separately connected to the generator 18 and permits attachment to the patient's skin surface to complete the circuit necessary for the application of RF energy as described below. A pair of wires 22b is connected to a temperature sensor 30 located on or in the electrode 28. Typically, the temperature sensor 30 will be a thermocouple consisting of a pair of dissimilar metals, usually copper and constantan which form a T-type thermocouple. The thermocouple wires 22b will also be connected to the radiofrequency generator 18 through the connector 24 and cable 26 so that they will be connected and disconnected as the catheter 12 is plugged and unplugged. The wires 22b may be utilized to verify the electrical continuity of the thermocouple.

The catheter 12 may optionally include additional electrodes 32 axially spaced apart over the distal end 14. Electrodes 32 will usually be provided to permit ECG monitoring prior to, during, and/or after the radiofrequency ablation treatment. Additional connectors (not illustrated) will be provided so that the electrodes 32 may be connected to external monitoring equipment (not illustrated) through the connector 24 and cable 26. Usually, the radiofrequency generator 18 will include provisions for connecting such monitoring equipment to the catheter 12. Optionally, the electrodes 32 may be used to perform initial mapping to locate the accessory pathways in a generally conventional manner. These aspects of the catheter, however, do not relate directly to the present invention and will therefore not be described in detail.

Catheter 12 preferably includes a deflectable distal tip which permits deflection, as illustrated in broken line in FIG. 2. A variety of control mechanisms (not illustrated) may be provided to effect such tip deflection as described generally in the medical and patent literature. Preferred tip deflection mechanisms are described in copending application Ser. Nos. 07/866,383 and 07/867,241, the disclosures of which are incorporated herein by reference.

Figure 4:
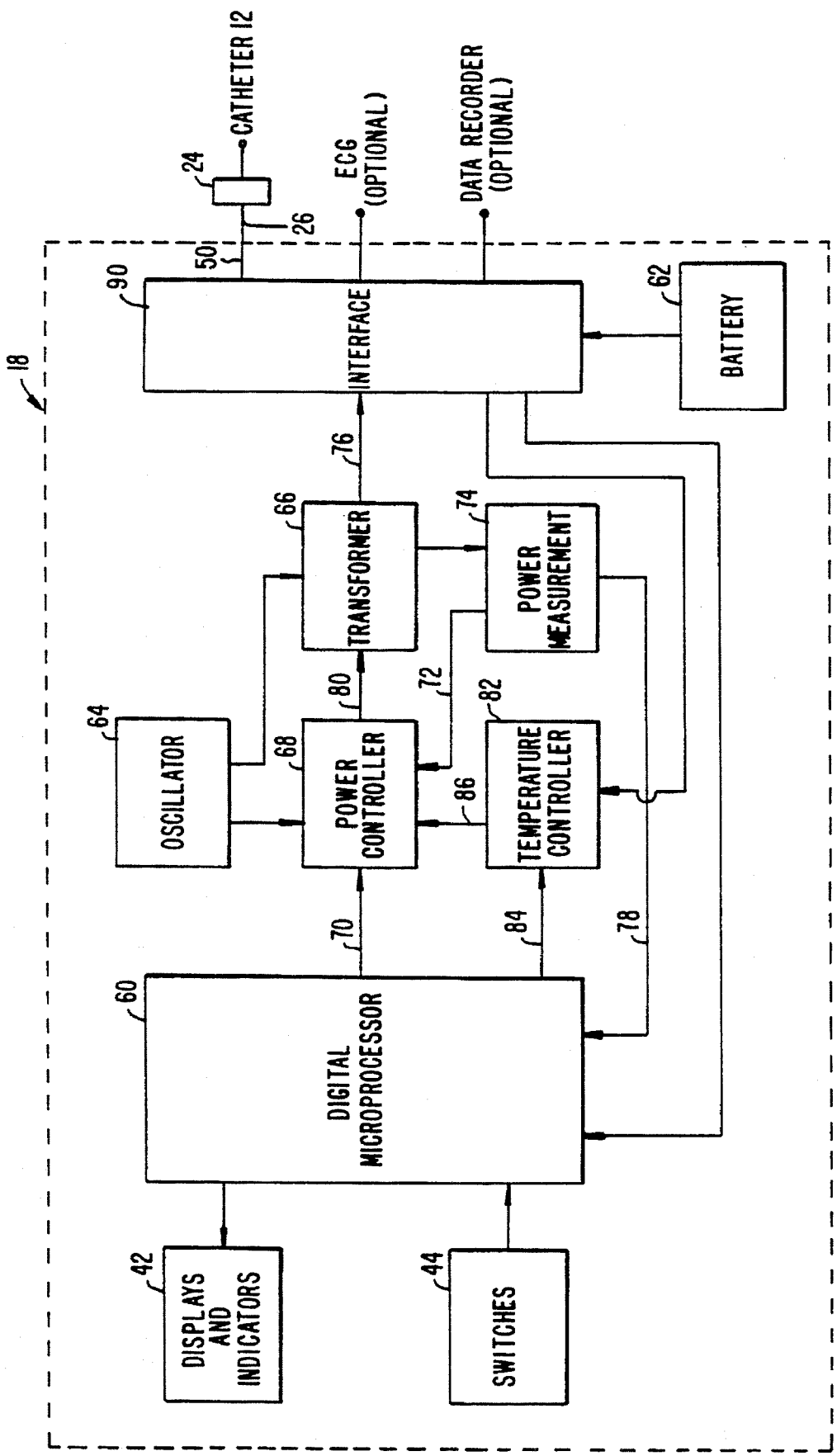
FIG. 4 is a block diagram of the circuitry of a radiofrequency generator constructed in accordance with the principles of the present invention.
Figure 5:
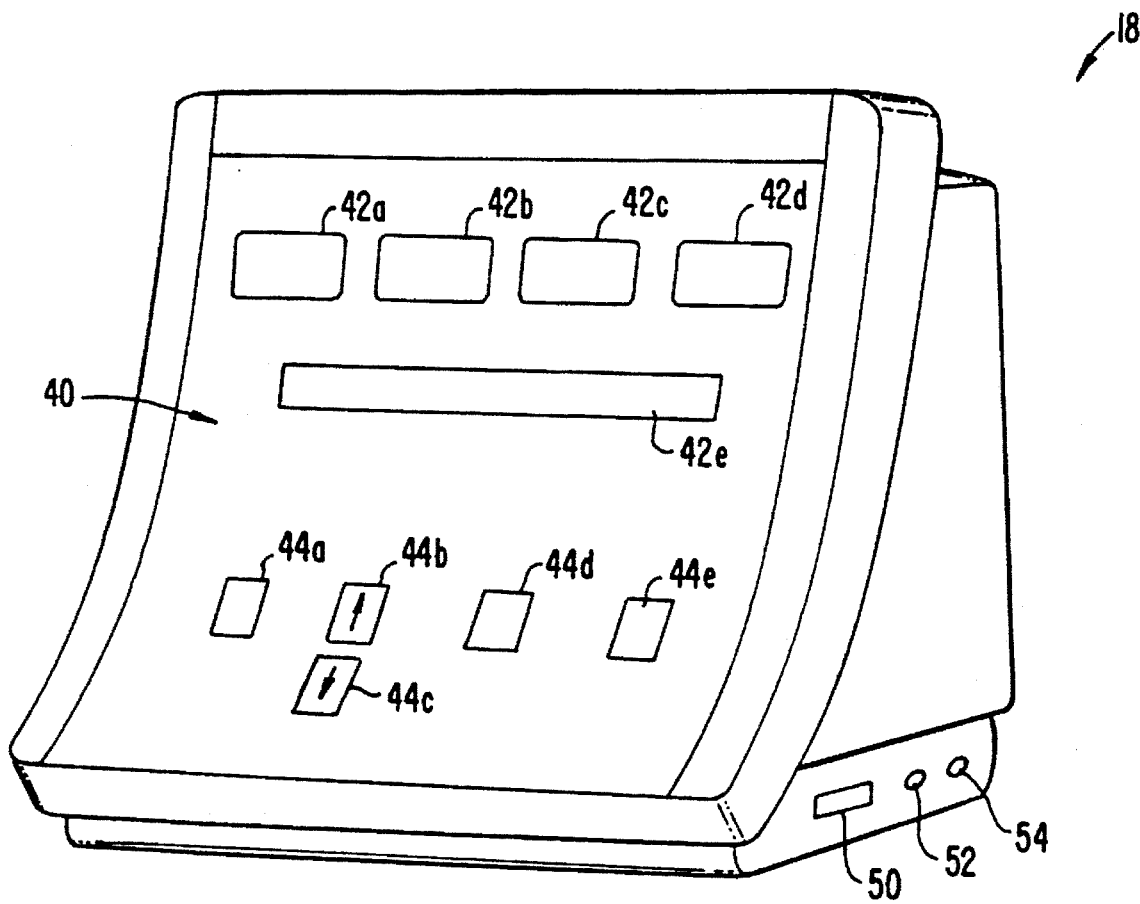
FIG. 5 illustrates the exterior of a power supply system constructed in accordance with the principles of the present invention.

Referring now to FIGS. 4 and 5, the radiofrequency generator 18 of the radiofrequency ablation system 10 will be described in more detail. Radiofrequency generator 18 includes a user interface panel 40 having a plurality of displays and indicators 42, switches 44 and legends (not illustrated), to permit the operator to monitor and control delivery of power to the catheter 12, as will be described in greater detail hereinafter. In particular, the indicators 42 and switches 44 permit monitoring and control of the amount of radiofrequency power delivered to the catheter 12 by radiofrequency generator 18. The panel 40 includes a first display 42a which provides a continuous digital readout of the actual radiofrequency power being delivered (usually calibrated in Watts). A second display 42b shows the actual electrode temperature measured by the thermocouple 30 (FIG. 3). A third display 42c shows the calculated impedance (based on measured current and voltage) between the catheter ablation electrode 28 and an indifferent electrode during the delivery of radiofrequency energy. The indifferent electrode is attached to the patient and provides a return path to complete the circuit to the tip electrode 28. A sudden rise in impedance indicates that coagulum has formed on the tip, which should be removed. A fourth display 42d provides an indication of the time that radiofrequency power has been delivered during an ablation procedure.

The panel 40 further include an alphanumeric display 42e which presents additional information to the user, depending on the operational mode selected as described below. Such information includes the set point for either temperature (in °C.) or power (in Watts), depending on the control mode. The display 42e can further set forth the total number of cycles, i.e. the number of times that power supply to the ablation electrode 28 has been initiated. The display 42e can further indicate total treatment time, i.e. the total elapsed time that the radiofrequency power has been delivered from the time power to the generator 18 was turned on. Finally, the legend 42e will indicate the available set point range for power, temperature, or time, depending on the variable which is being set within the system (when a set point is changed).

The alphanumeric 42e can further provide user warnings, including excessively high temperature, unacceptable catheter (when an open circuit in the catheter is detected during a radiofrequency generator verification check, as described below), excessively high impedance, low impedance, and excessively high power. Finally, a legend (not illustrated) will indicate when the battery charge has become low, typically when it reaches 25% of capacity. Conveniently, a tone warning signal will be provided whenever any warning is being displayed.

A switch 44a is provided in order to select the control mode, i.e., either power or temperature. A particular variable (temperature or power) will be adjusted by raising or lowering the set point using the appropriate up or down switch 44b or 44c. The user presses and holds switch 44d and increases the time set point by pressing switch 44b or decreases the time set point by pressing switch 44c. After initiation, the power will be delivered for the total time thus set. The value of the particular variable set point (and allowable range) is displayed on alphanumeric display 42e as the set point is being adjusted.

Switch 44e controls the delivery of RF power. When the RF power generator 18 is first turned on, a legend OFF (not illustrated) is lit. Switch 44e must be pressed to put the unit in standby which also activates an optional foot pedal (not illustrated). Once in standby mode, pressing switch 44e causes RF power to be delivered until either the switch 44e is again pressed or the time set-point is reached, at which time the unit returns to standby. If a warning condition occurs (i.e., high power or high impedance), the unit goes to OFF mode and the optional foot pedal is deactivated.

A main off and on switch is provided on the top of the radiofrequency generator 18. A catheter connector 50, an indifferent electrode connector 52, and a foot pedal connector 54 are provided on the right side of the radiofrequency generator 18. The catheter connector 50 permits plugging in of the catheter connector 24 to cable 26 to provide the necessary connections between the electrical components of the catheter and the generator 18. The foot pedal connector permits connection of a pneumatic foot pedal which allows the treating physician to control the application of radiofrequency power by depressing and holding the foot pedal.

Additional connections on the radiofrequency generator 18 will usually include an ECG connector, an analog output connector which permits output to a multi-channel chart recorder for recording radiofrequency power, impedance between the ablation electrode and indifferent electrode, and ablation electrode temperature. An additional connector will usually be provided to permit connection of the internal microprocessor to an external computer to monitor and temporarily override programming in the PROMS. The connector will usually be a conventional RS-232 connector which is compatible with standard IBM-type personal computers. A switch may also be provided to permit the operator to set the volume level of the tone during the RF ablation. Finally, a TUV connector will be provided for connection to an external ground.

Referring now to FIG. 4 in particular, the front panel displays and indicators 42 and switches 44 will be connected to a digital microprocessor 60, such as an INTEL 80C 186, which permits interface between the user and the remainder of the electrical components of the system. In particular, the microprocessor 60 provides for continuous monitoring of power, current, voltage, temperature, impedance, and battery level. As necessary, the microprocessor will provide this information to the appropriate display and/or indicator 42 on the front panel 40. Additionally, the microprocessor 60 permits the user to select the control mode (either constant temperature or constant power) and to input the power set point, temperature set point, and timer set point to the system.

The primary source of power for the radiofrequency generator 18 is a battery 62, typically a 12 V battery rated at 7.2 ampere-hours. A back-up battery (usually a lithium cell; not illustrated) will be provided to provide sufficient power to the microprocessor 60 to maintain desired memory functions when the main power from battery 62 is shut off.

A crystal-locked radiofrequency oscillator 64 generates the switching pulses which drive both the power transformer 66 and the power controller 68. Power controller 68 is an analog controller which operates by pulse-width modulation by comparing a power set point signal 70 (from microprocessor 60) with an actual power signal generated by a power measurement circuit, typically a torroidal transformer coupled to the power output 76 from the transformer 66. The power measurement component 74 multiplies the output current and voltage and provides the resulting actual power signal to both the power controller through line 72 and the microprocessor through line 78. Separate analog comparator circuits (not illustrated) are provided for monitoring the output of the power measurement component 74 in order to shut-off current to the output transformer if the power exceeds a limit, typically 55 watts.

Power transformer 66 includes a center tap which receives the output 80 of the analog power controller 68. Secondary winding provides for continuous monitoring of the applied voltage in order to permit the power calculations by power measurement circuit 74.

Figures 12, 12B:
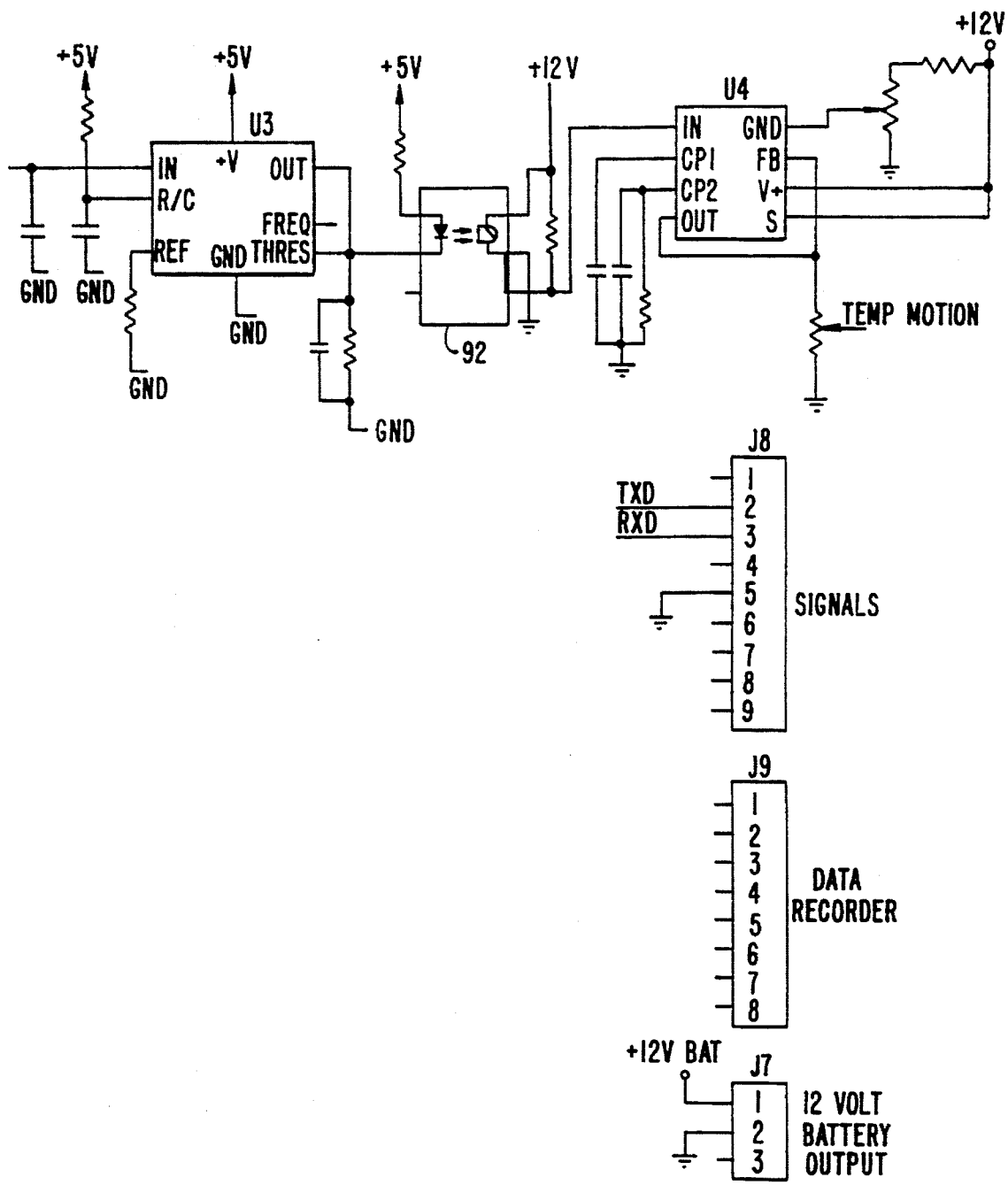
Figure 12A:
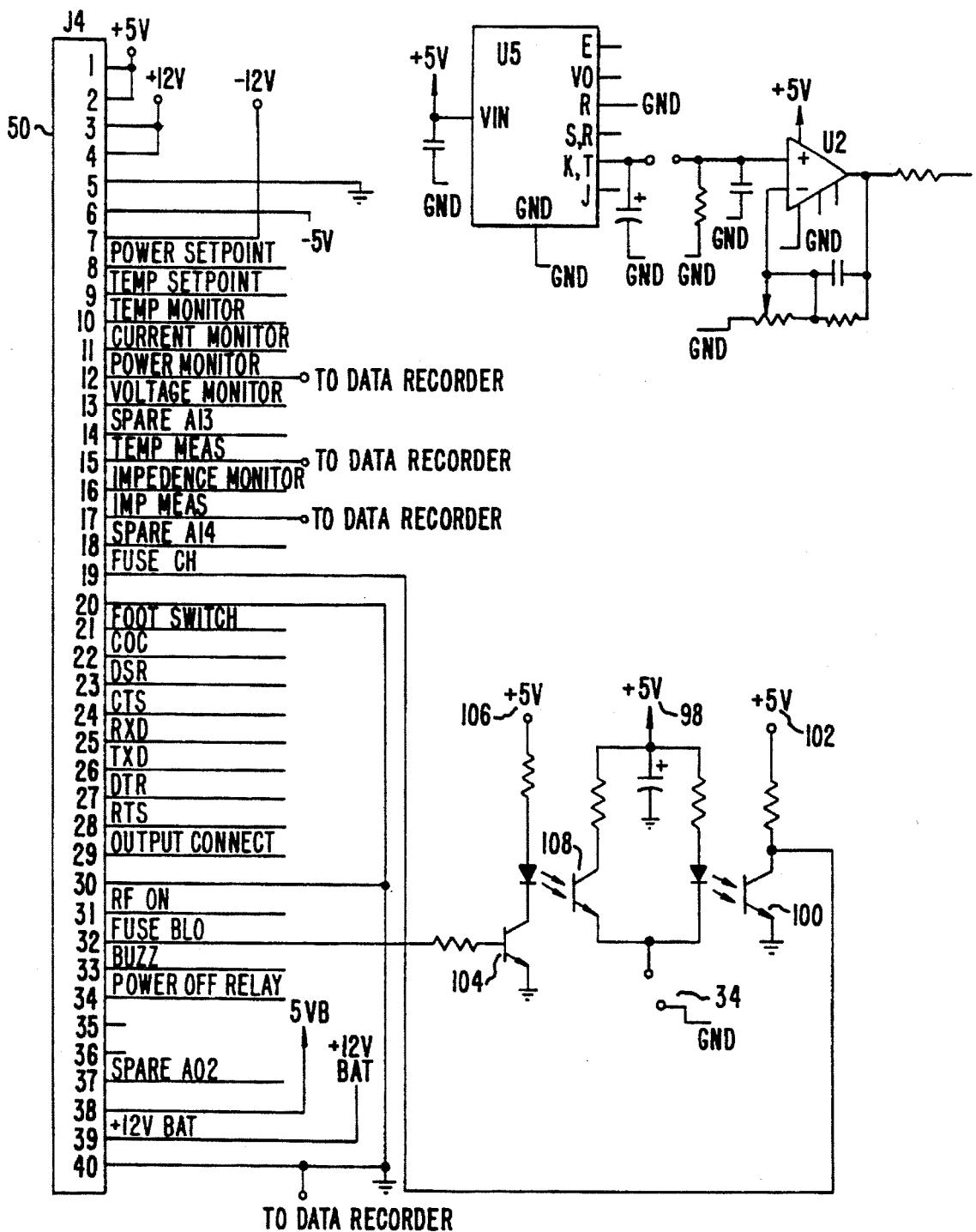
Figure 12C:
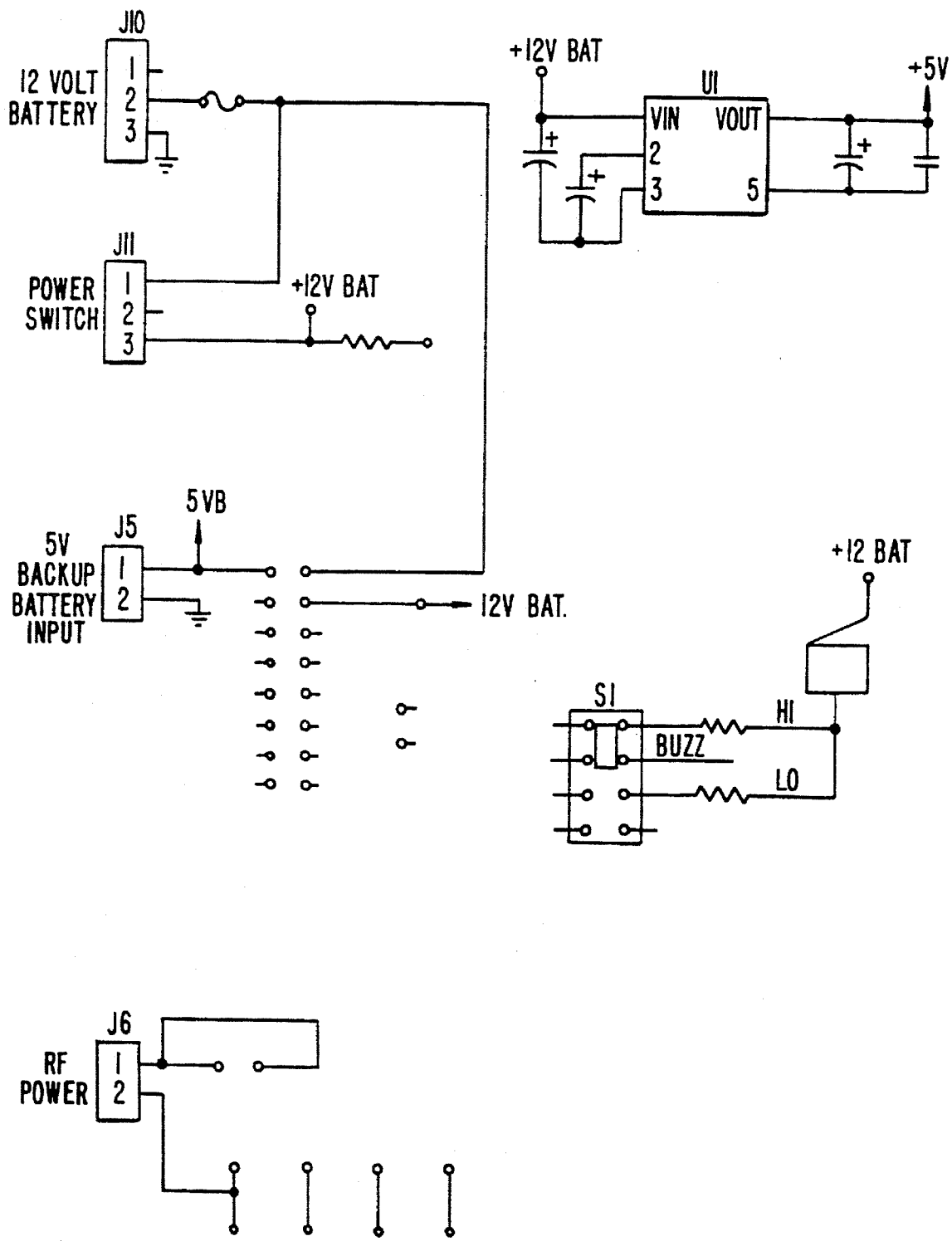

In a preferred aspect of the present invention, an analog temperature controller 82 is provided to permit operation in a temperature control mode. A temperature set point is delivered to the temperature controller 82 from the microprocessor 60 through line 84. Analog controller 82 operates on a proportional control mode, producing a power set point 86 which is fed to the power controller 68. Power set point 86 replaces the set point 70 when the system is in temperature control mode operation. The analog power controller 68 thus acts as a cascade control loop in a two-stage temperature control protocol. It has been found that such two-stage analog control permits precise and very fast control of power to maintain the desired temperature set point at the ablation electrode 28. In particular, the control scheme permits very rapid temperature rise to the desired temperature set point with minimum overshoot and very close temperature maintenance throughout the duration of the radiofrequency ablation cycle. The temperature will usually be maintained within ±5° C. of the set point, more usually being maintained to within ±2° C. of the set point. Separate analog comparator circuits 90, illustrated in FIG. 12, are provided for monitoring the temperature of the thermocouple 30 in order to shut-off current to the output transformer if the temperature exceeds a limit, typically about 100° C.

All external connections to the radiofrequency generator 18 will be made through an interface board 90. The interface board 90 permits connection of the main battery 62 and back-up battery (not illustrated), as well as the catheter connector 50, the ECG connector, the data recorder connector, and the like. Connection of the thermocouple will be optically isolated from the internal components of the radiofrequency generator 18 by optoisolator 92, shown in FIG. 12. The data recorder outputs on the RF generator 18–94 may be optically isolated if necessary to reduce signal noise. Such isolation provides both patient safety as well as isolation of the internal components of the generator 18 from the radiofrequency power which is being delivered to the patient.

The detailed circuitry necessary to construct the radiofrequency generator 18 is set forth in detail in the appendix attached to this application. The appendix includes six circuit diagrams, where each circuit diagram is labeled to indicate the components which are included on that diagram.

In the embodiment described above, the RF signal is a square wave signal. However, some operating environments require that the square wave generated by the crystal-locked radiofrequency oscillator 64 be filtered to round off the square edges to provide a sinusoidal instead of pulsed RF signal. At high-power this filtering causes undesirable signal attenuation. An alternative power modulating system that obviates the need for filtering and is particularly useful for high-power applications is depicted in FIG. 13.

High power is required for the ablation of Ventricular Tachycardia (VT) sites of origin, located in the ventricles. Since the ventricles are the heart's largest and most important pumping chambers VTs can be more life threatening and less easily tolerated than SVTs. In particular, an Ischemic VT is caused by a prior myocardial infarction (MI), or heart attack. In a heart attack, oxygenated blood flow to a region of heart muscle is interrupted for a period of time long enough to cause death or injury. This flow interruption is commonly caused by an obstruction or spasm in one the heart's coronary arteries. Following an MI, the area of dead tissue typically becomes covered by protective scar tissue. In addition, a border zone of mixed dead and live tissue surrounds the dead area.

When the wave of electrical propagation travels through this region of the ventricle, multiple "Micro Reentry Circuits" can occur, causing acceleration of the ventricular beat. Thus, the challenges in ablating these VT sites of origin are as follows: 1) multiple sites are difficult to locate, may cover significant areas, and additional "masked" sites may become evident following ablation of dominant sites; 2) scar tissue can make delivery of RF energy sufficient to cause ablation of underlying sites of origin very difficult; and 3) Micro- and Macro-Reentry Circuits may be located deep in the heart wall making delivery of sufficient RF energy for ablation difficult. Thus, higher power may improve the success rate for Ischemic VT ablation because high power should permit the creation of larger, deeper lesions.

Figure 13:
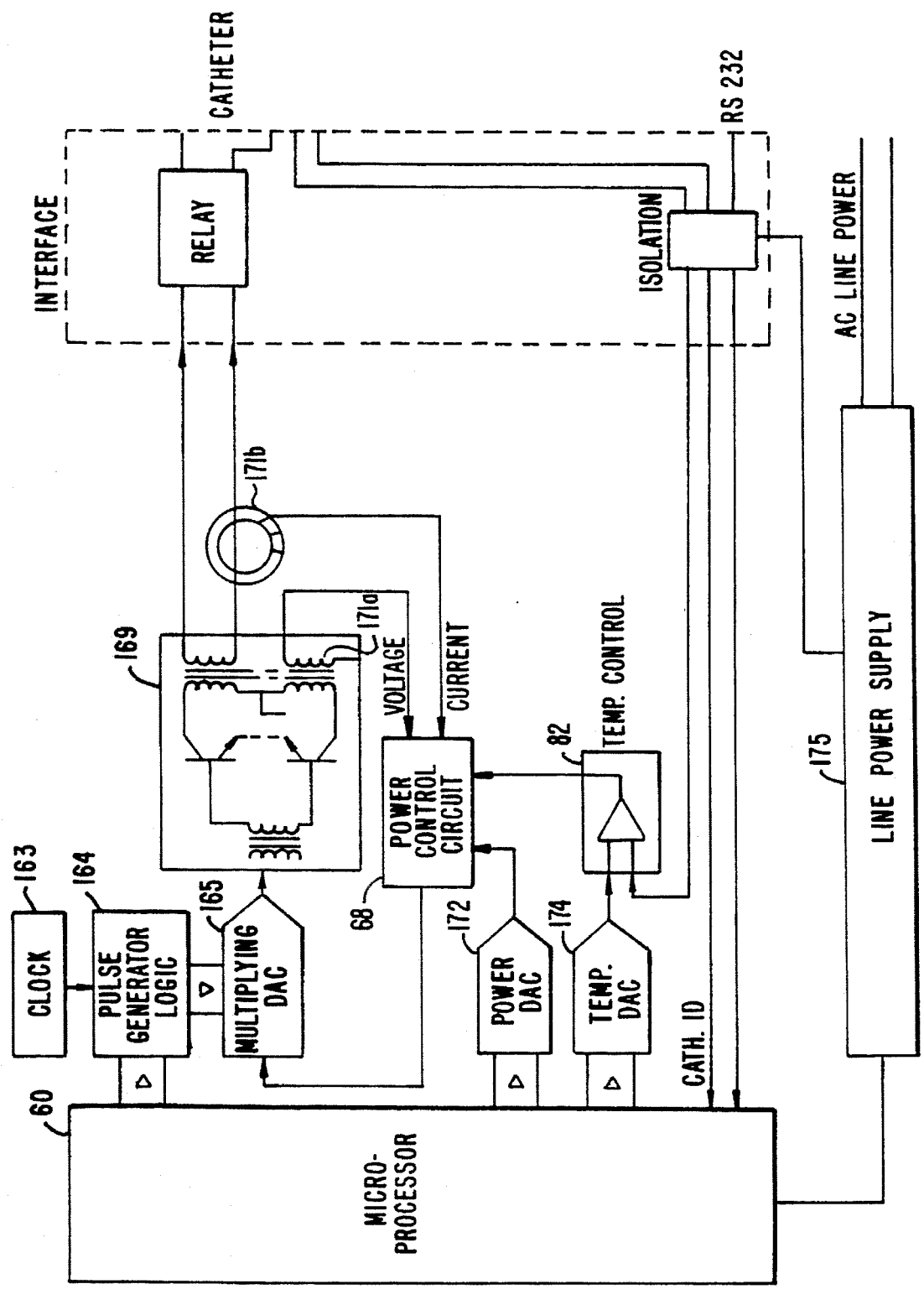
FIG. 13 is a block diagram of the circuitry of a radiofrequency generator utilizing a multiplying DAC to modulate the radiofrequency power signal.

In FIG. 13, a clock 163 and pulse generator logic 164 provides a digitized sinusoidal RF signal. This signal is provided to the digital input of a multiplying digital to analog convertor (DAC) 165 having its reference voltage input coupled to the analog control output of the power controller 68. The analog output of the multiplying DAC 165 is coupled to power amplifier and transformer control circuit 169. Power controller 68 also has an actual power measurement input coupled to the power amplifier via coupling transformers 171a and b, a first power set point input coupled to the control output of a temperature controller 82, and a second power set point input coupled to microprocessor 60 by DAC 172. In addition to its control output, temperature controller 82 has a temperature set point input coupled to microprocessor 60 by DAC 174 and an actual temperature input coupled to receive an actual temperature signal generated by the temperature sensor 30 in the catheter tip.

The operation of the analog power and temperature controllers 68 and 82 is the same as described above with reference to FIG. 4. In the temperature sensing mode the controllers act as a cascade control loop with the temperature controller 82 generating the power set point signal proportional to the difference between the magnitude of the temperature set point and the actual temperature signal and the power controller 168 generating a power output signal proportional to the difference between the magnitudes of the power set point and the actual power signal.

The multiplying DAC 165 converts the received digital RF sinusoidal signal to an analog RF sinusoidal having an amplitude proportional to the magnitude of the power output signal. Because the RF power signal is sinusoidal, the energy dissipation problem associated with filtering pulsed RF power signals is avoided.

One problem associated with delivery of high power RF energy from the catheter in vivo is the formation of coagulum on the tip. As RF power is delivered to tissue the tissue heats up. When this heat is transferred to the tip its temperature rises and blood begins to coagulate on the tip as its temperature approaches 100° C. This coagulum on the tip causes a significant increase in impedance which dramatically reduces the ability of the electrode to deliver RF energy to the tissue.

In the embodiment of FIG. 13, the temperature control feature is utilized to maintain the tip temperature below 100° C. However, as described above, temperature control functions to limit the RF energy delivered to the tissue. Thus, in addition to temperature control the microprocessor 60 controls the pulse generator logic 165 to pulse the sinusoidal RF power signal which may provide further benefit in preventing coagulum formation.

Figure 14:
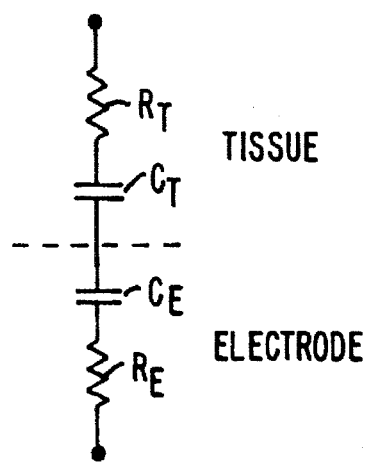
FIG. 14 is a schematic diagram illustrating the thermal characteristics of the tip and tissue to be ablated.

This benefit is illustrated by FIG. 14 which is a thermal circuit diagram modelling the catheter and tissue to be ablated. A capacitor represents the heat storage capability and a resistor represents the heat transfer capability of the thermal circuit elements. By analogy to electrical circuits, the product of resistance and capacitance (RC) is a time constant indicating the rate at which temperature changes when heat is applied to the circuit. The time constant of the tip is small because metal changes temperature very quickly. In contrast, the time constant of the tissue is larger because it changes temperature more slowly than metal. Accordingly, a high energy RF pulse will energize the tissue to cause a lesion. However, the temperature of the tip will decrease rapidly between pulses because of the low RC constant for the tip thereby keeping the tip temperature below 100° C. to avoid the formation of coagulum.

Thus, the pulsing and temperature control cooperate to allow the efficient transfer of high energy from the tip to the tissue. The temperature control increases the amplitude of the RF sine wave to converge on the set temperature while the pulsing helps prevent temperature increase at the tip.

Figure 15:
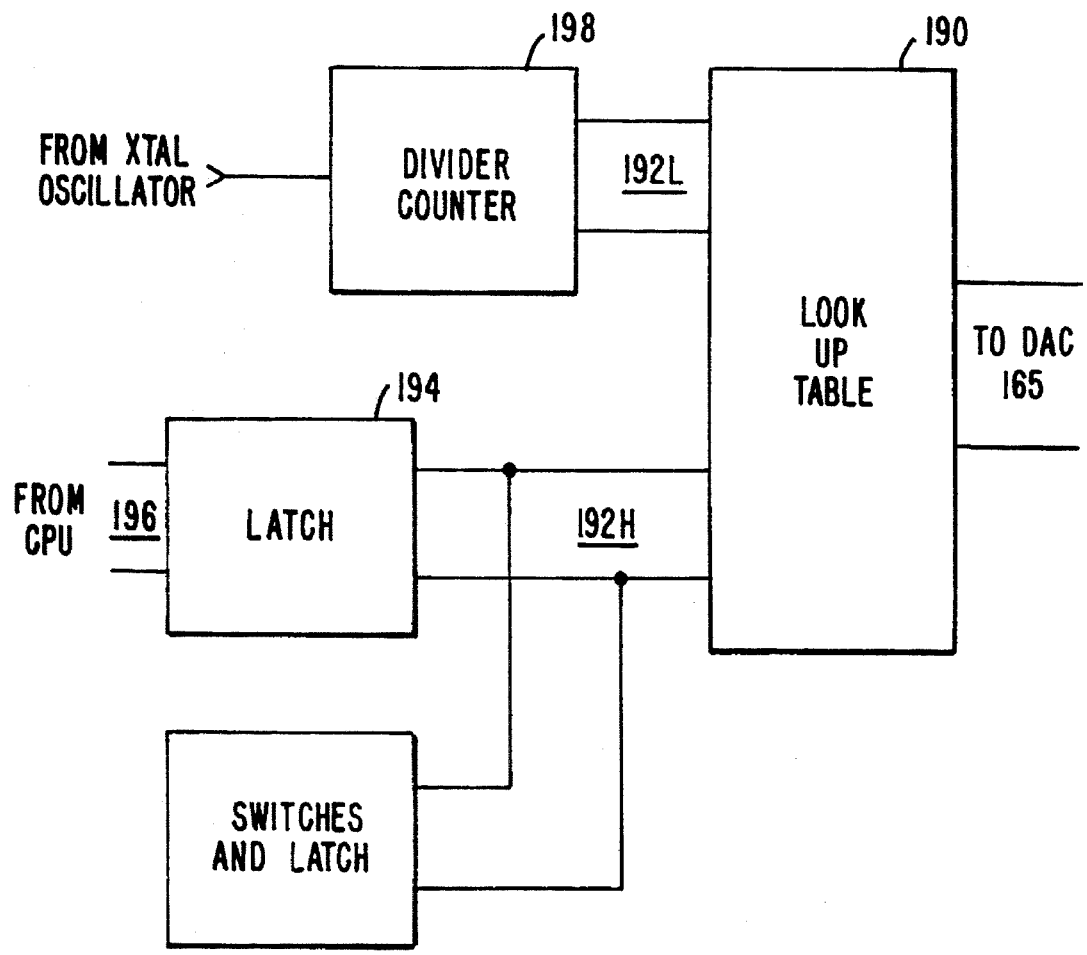
FIG. 15 is a block diagram of the pulse generating circuit.

The structure of the pulse generator logic circuit 164 is depicted in FIG. 15. As described above with reference to FIG. 13, the RF energy can be pulsed to allow the ablation of larger lesions while avoiding the build-up of coagulum on the tip. Referring now to FIG. 15, a look up table (LUT) 190 stores the values of a sinusoidal signal in storage locations accessed by a first part of the LUT address space and stores zeroes in storage locations of a second part of the address space.

The LUT address bus 192 has its higher order bit lines 192H coupled to the output of an address latch 194. The input of the address latch 194 is coupled to the data bus 196 of the CPU 60. The lower order bit lines 192L of the address bus 192 are coupled to the output of a DIVIDER/COUNTER 198 which outputs a count value being continuously incremented by the clock signal from the clock 163 and being reset at selected count values.

The operation of the pulse generator logic will now be described. During pulse mode operations the microprocessor 60 sets the higher order address bits in the address latch 194 to provide sinusoidal RF energy in pulses of a selected length interspersed with null energy intervals of selected length.

During an energy pulse interval high order address bits selecting the first part of the LUT address space are written to the address latch. The count output from the DIVIDER/COUNTER 198 then sequentially accesses successive storage locations to output the digital magnitudes of a sinusoidal function. These digital magnitudes are converted to an analog sinusoidal signal by the multiplying DAC 165 with the amplitude determined by the output of the power control circuit 68.

During a null energy interval high order address bits selecting the second part of the LUT address space are written to the address latch. A zero is output from the LUT 190 regardless of the count value output by the DIVIDER/COUNTER 198.

Figure 6A:
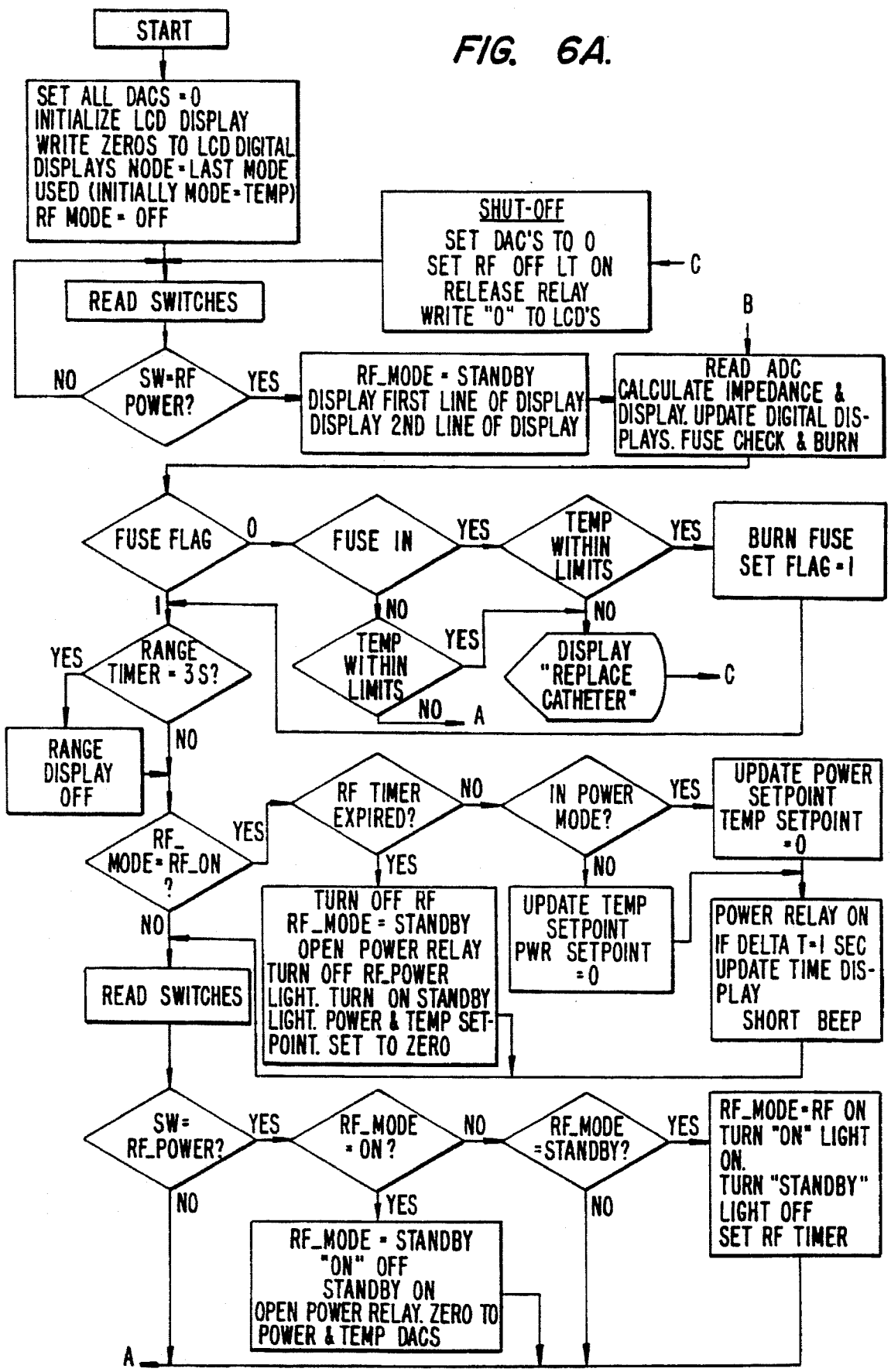
FIGS. 6A and B illustrate a flow chart of the operating program of the microprocessor-controlled power system of the present invention.
Figure 6B:
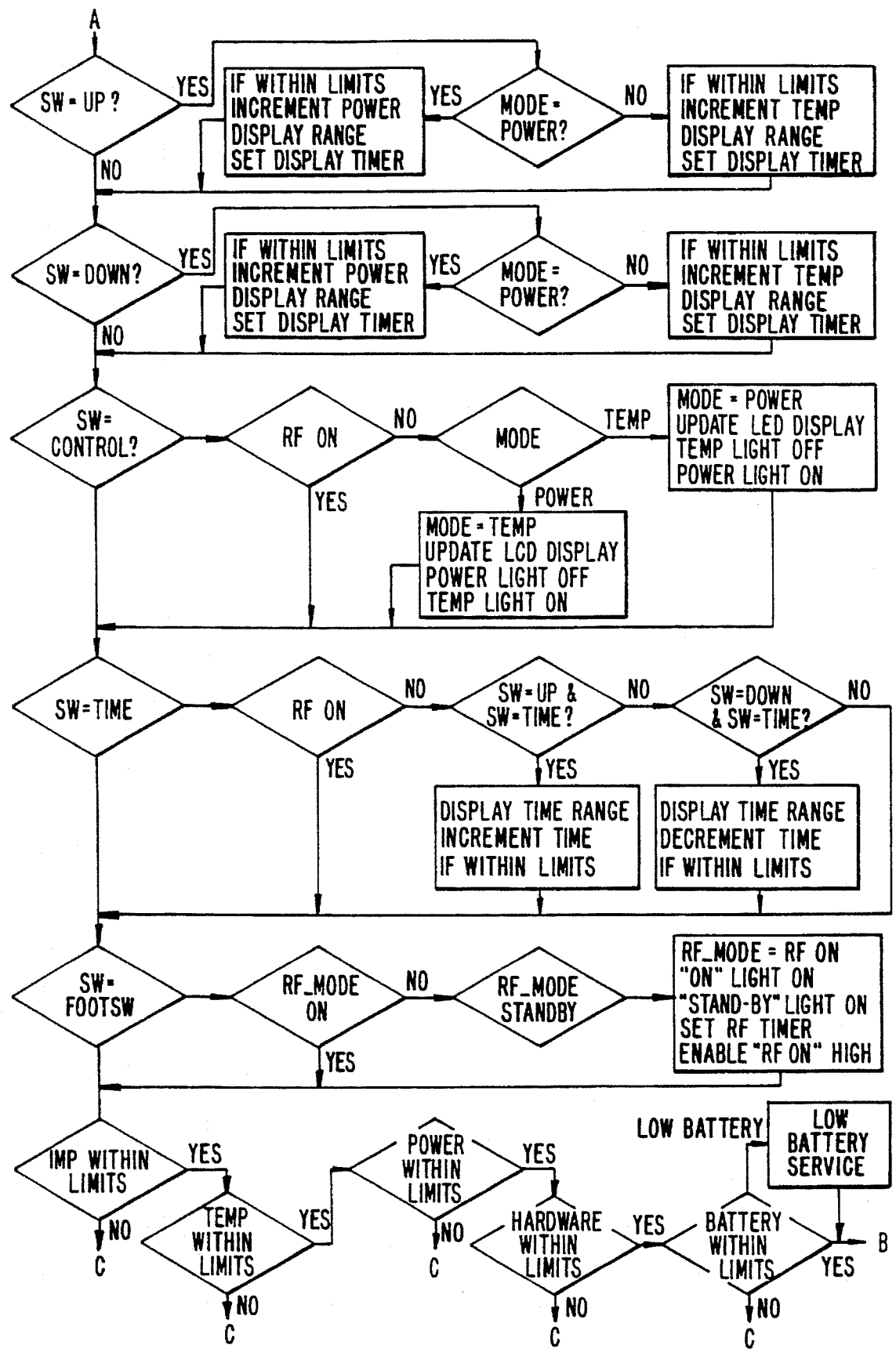

Operation of the microprocessor is schematically illustrated in the flow sheet included in FIGS. 6A and B.

The relationship of the microprocessor 60 to other hardware elements of the RF ATAKR system are shown in FIG. 4. The variable inputs to and outputs from the microprocessor 60 are identified as follows:

| MICROPROCESSOR | |
| --- | --- |
| From catheter 12: | To catheter 12: |
| Tip electrode temperature<br>Impedance (tip electrode to<br>indifferent electrode) | Power to tip |
| From power controller 68: | To power controller 68: |
| Power level<br>Voltage<br>Current | Start/stop RF power |
| From panel face 40: | To panel face 40: |
| Control mode<br>Temperature set point<br>Power set point<br>Timer set point<br>RF Power delivery | System status (on, off, standby)<br>Audible alarm<br>Visual alarm<br>Displays (power, temp., impedance, etc.) |

The microprocessor 60 performs the system control function by reading the user, catheter, and generator input values and providing corresponding power on/off commands to the RF power controller 68 and system status and alarm information to the user. The input values for temperature, current, and voltage originate as analog signals and are converted to digital (via digital/analog converters (DAC's)) for the microprocessor. Impedance and power are calculated from current and voltage. Timing is maintained by onboard clock.

Default values of the system are maintained in two ways. Preset default settings are in effect upon initial use and if the backup battery fails. These present default settings are as follows:

| Setting | Default Condition |
| --- | --- |
| Control Mode | Temperature |
| Temperature set-point | 70° C. |
| Power set-point | 20 Watts |
| Time set-point | 30 seconds |

If the user changes these settings, the last settings entered become the default settings on system power-up providing the backup battery does not fail.

Specific safety features incorporated in the programming of the microprocessor 60 include the following.

In both temperature and power control mode, RF power is applied to the catheter only during the selected cycle time and only when the impedance is within a preset range (typically 25 to 250 ohms). Additionally, power must be below a preset maximum (typically 55 watts maximum), and the temperature must be below a preset maximum (typically 50 to 105° C. when operating in temperature control mode). Also, the catheter must not have been previously used as described earlier.

Figures 7, 7F:
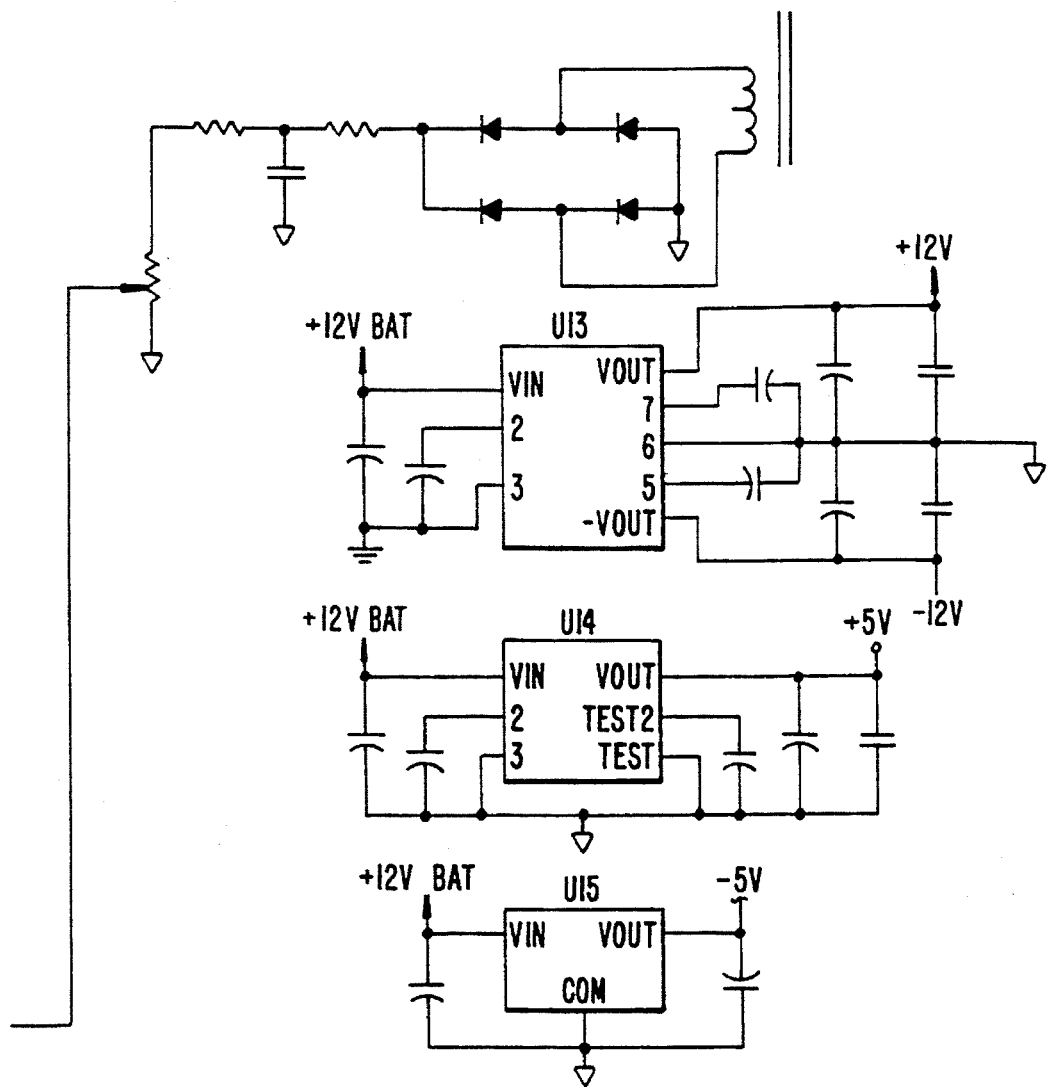
Figure 7A:
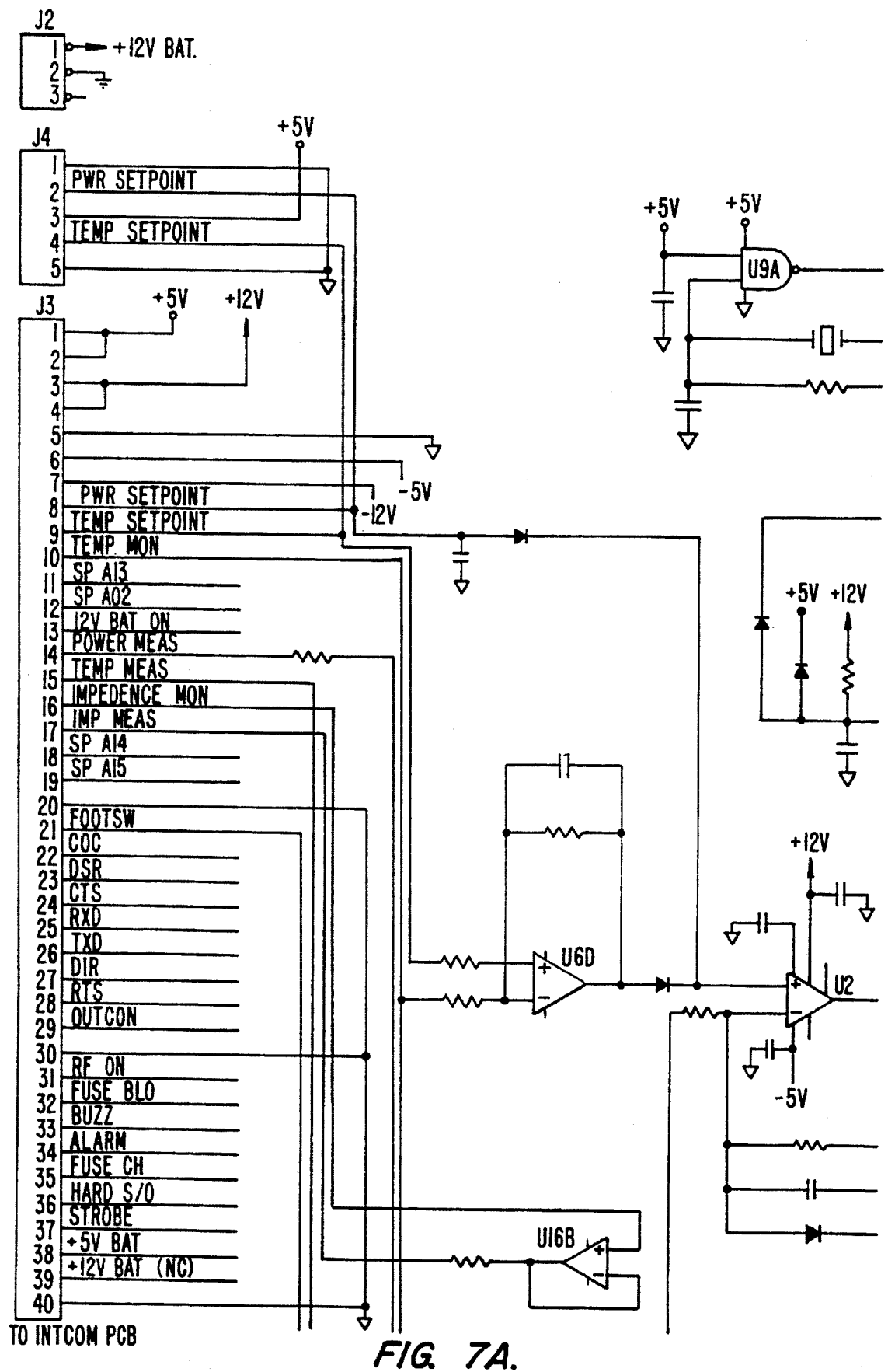
Figure 7B:
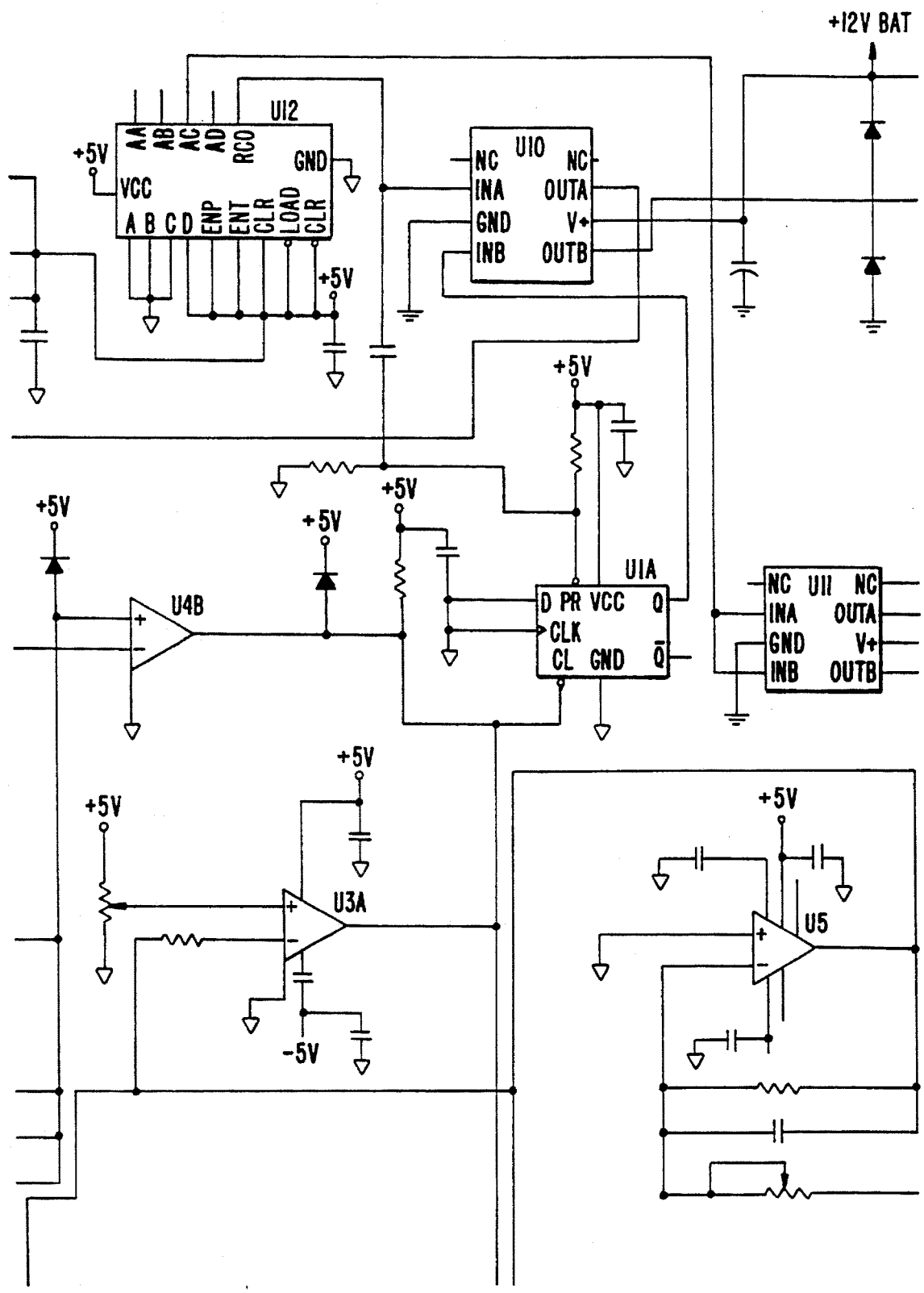
Figure 7C:
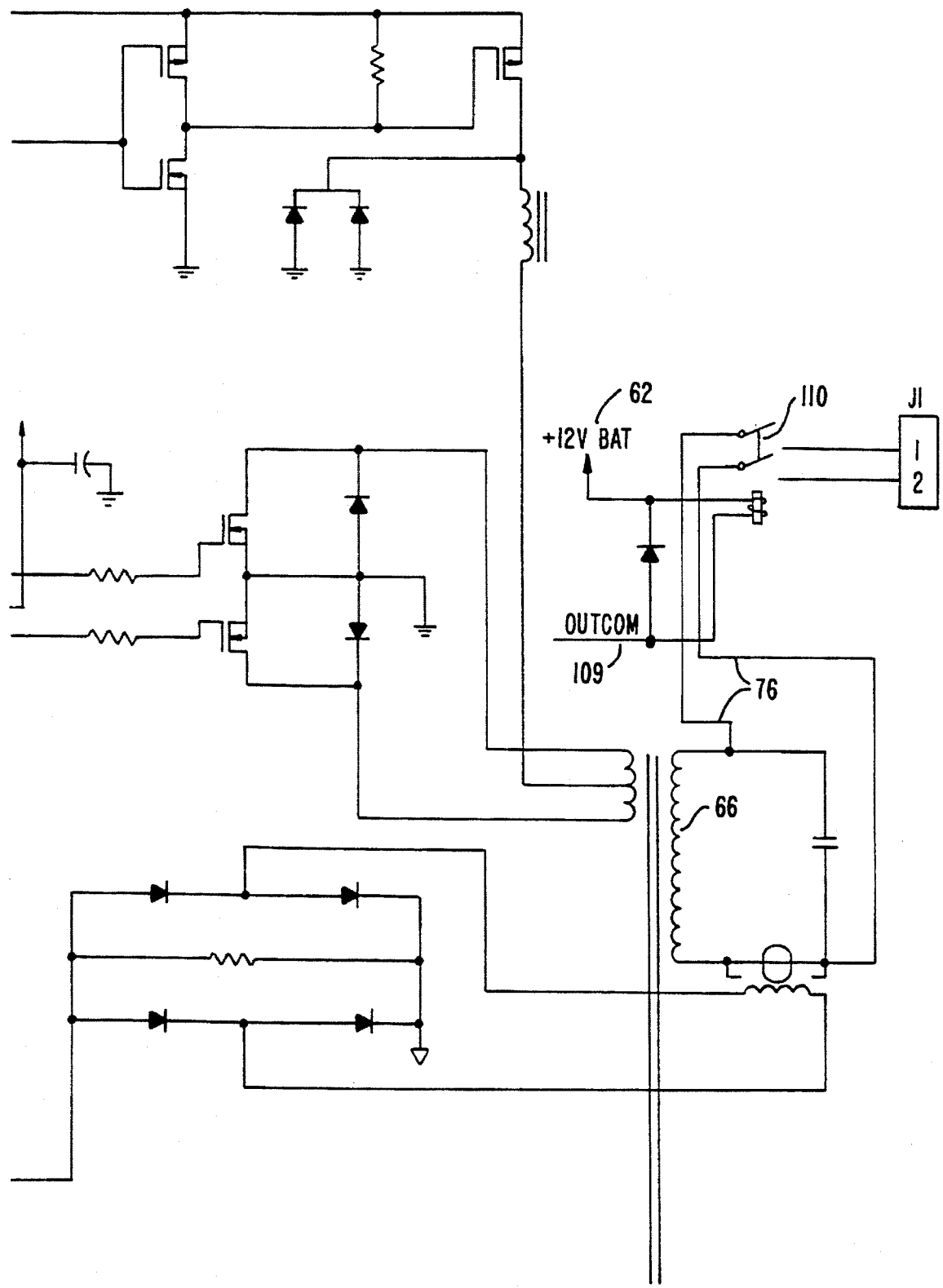
Figure 7D:
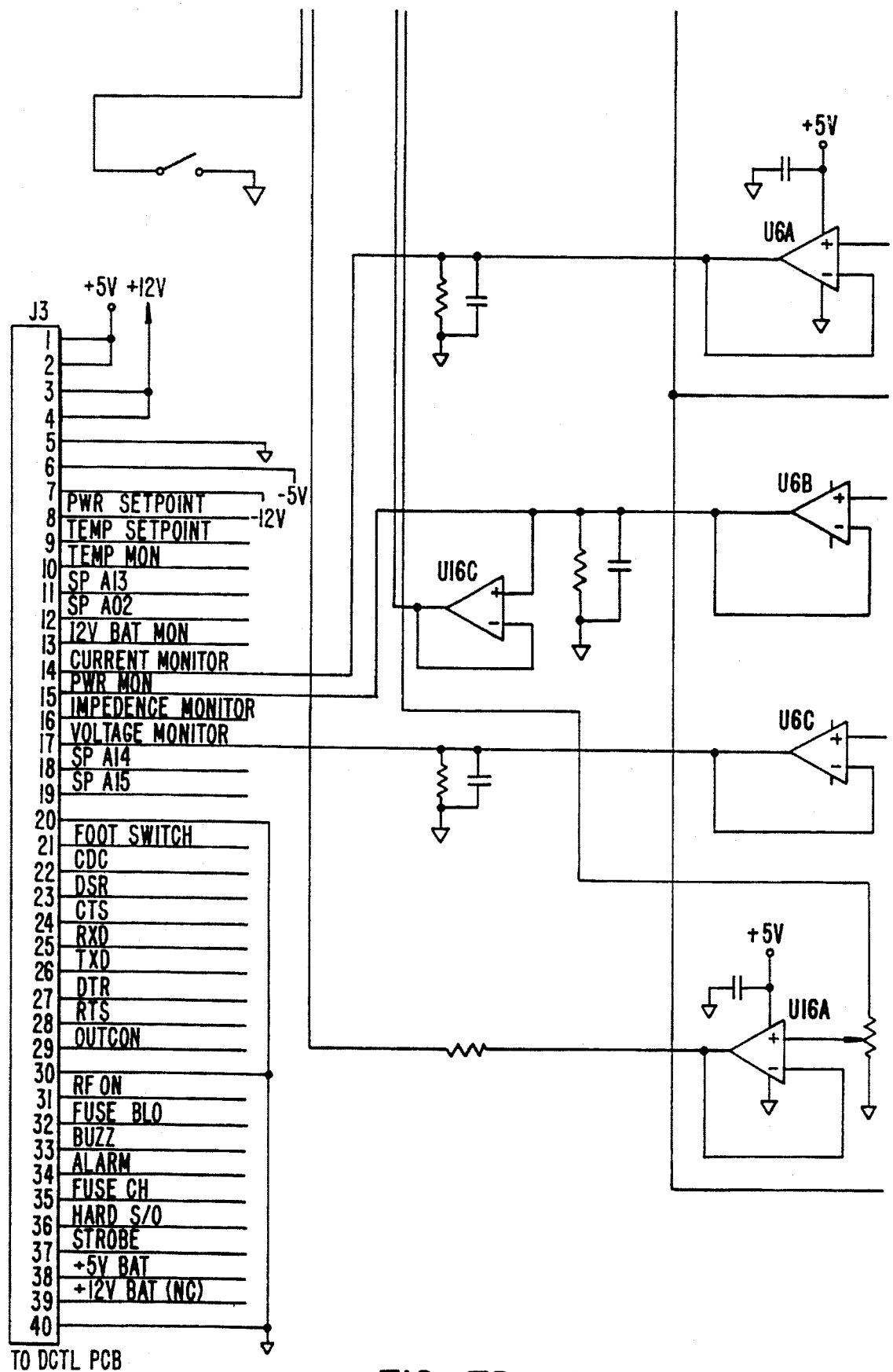
Figure 7E:
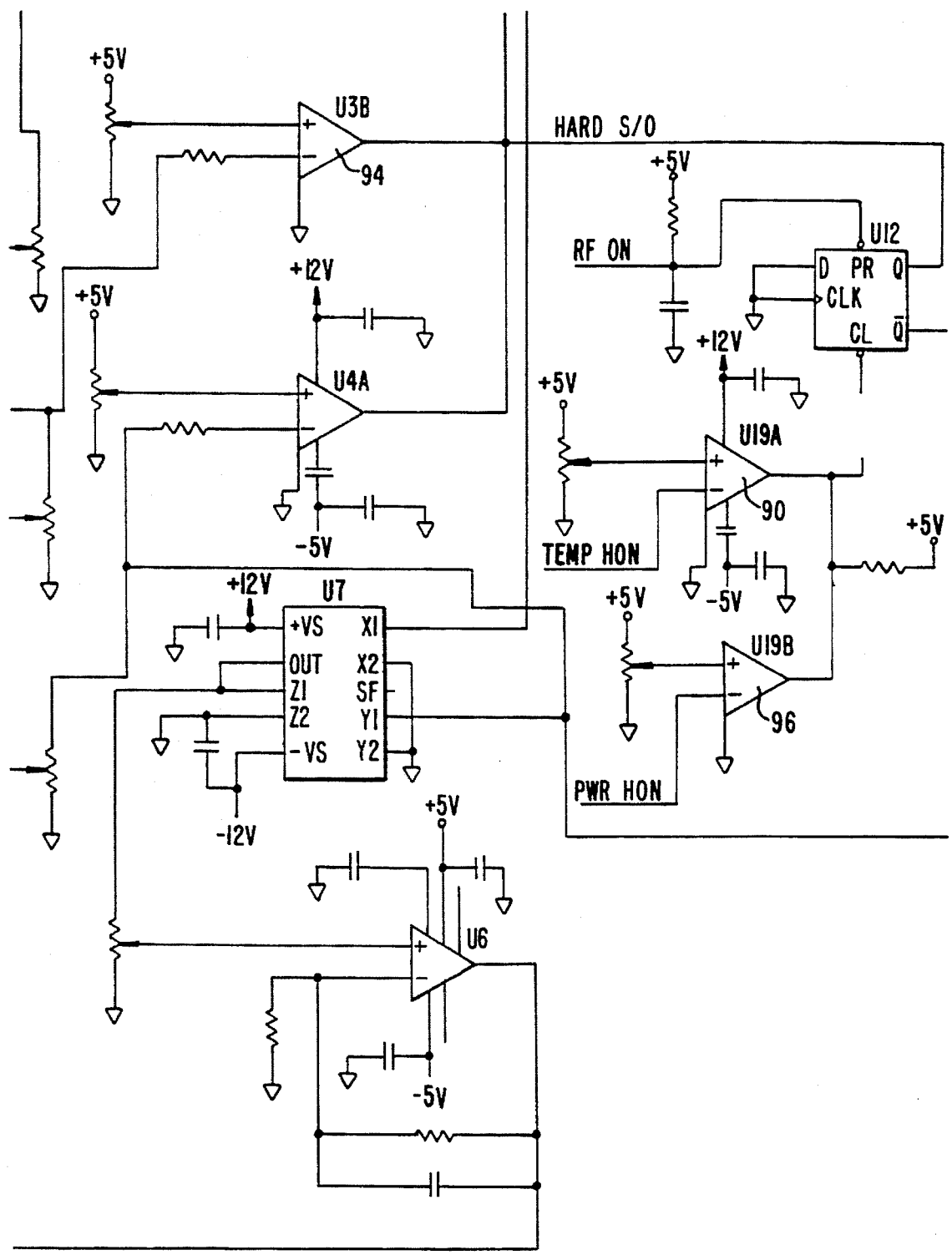
Figures 8, 8A:
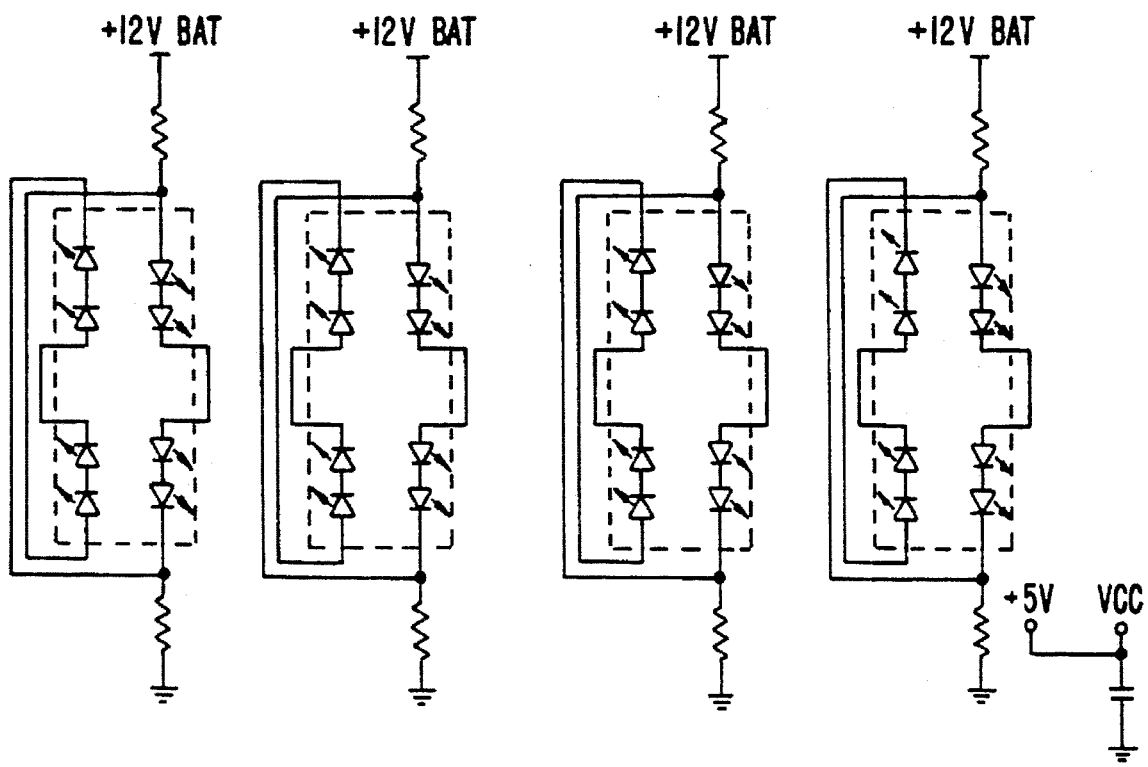
Figure 8B:
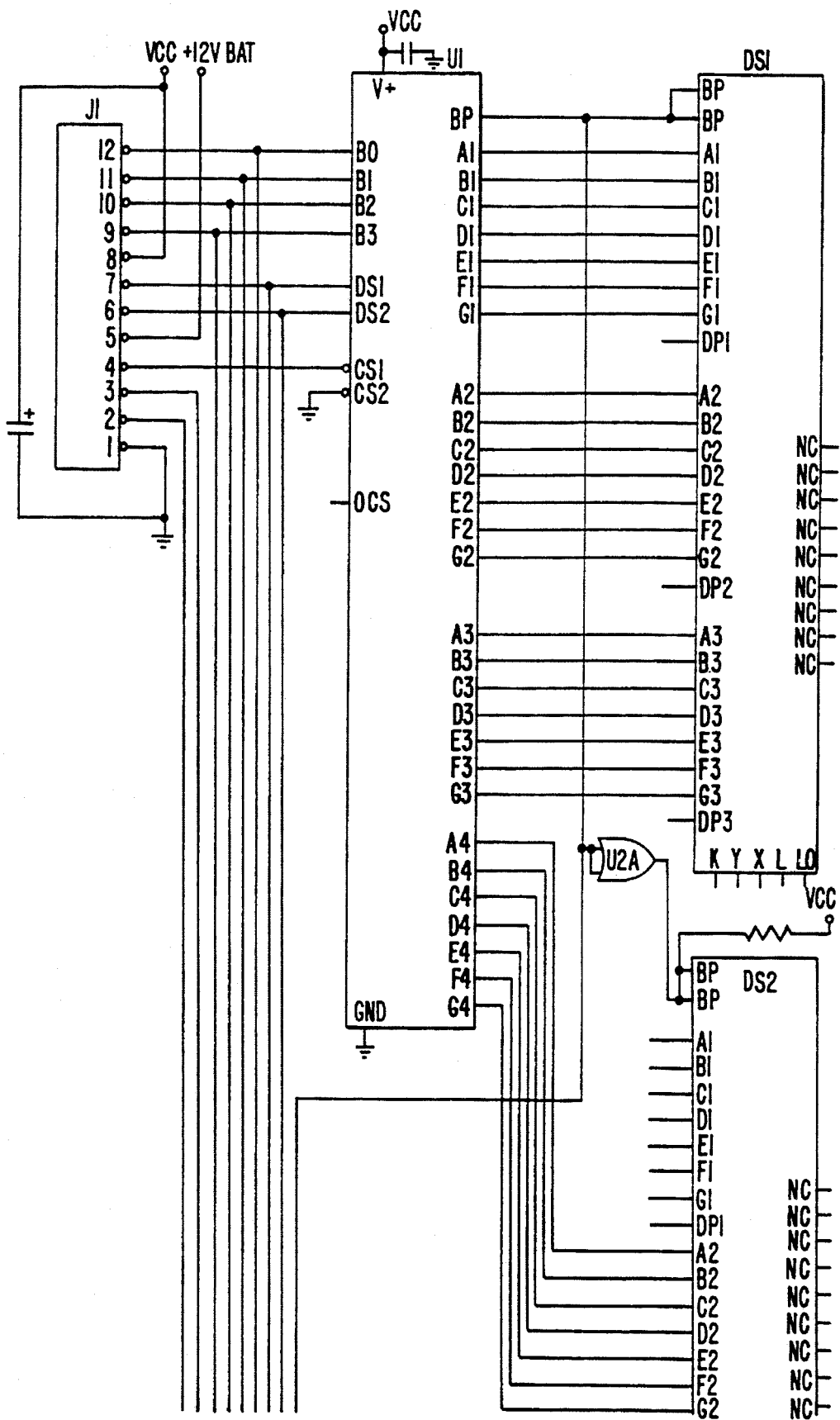
Figure 8C:
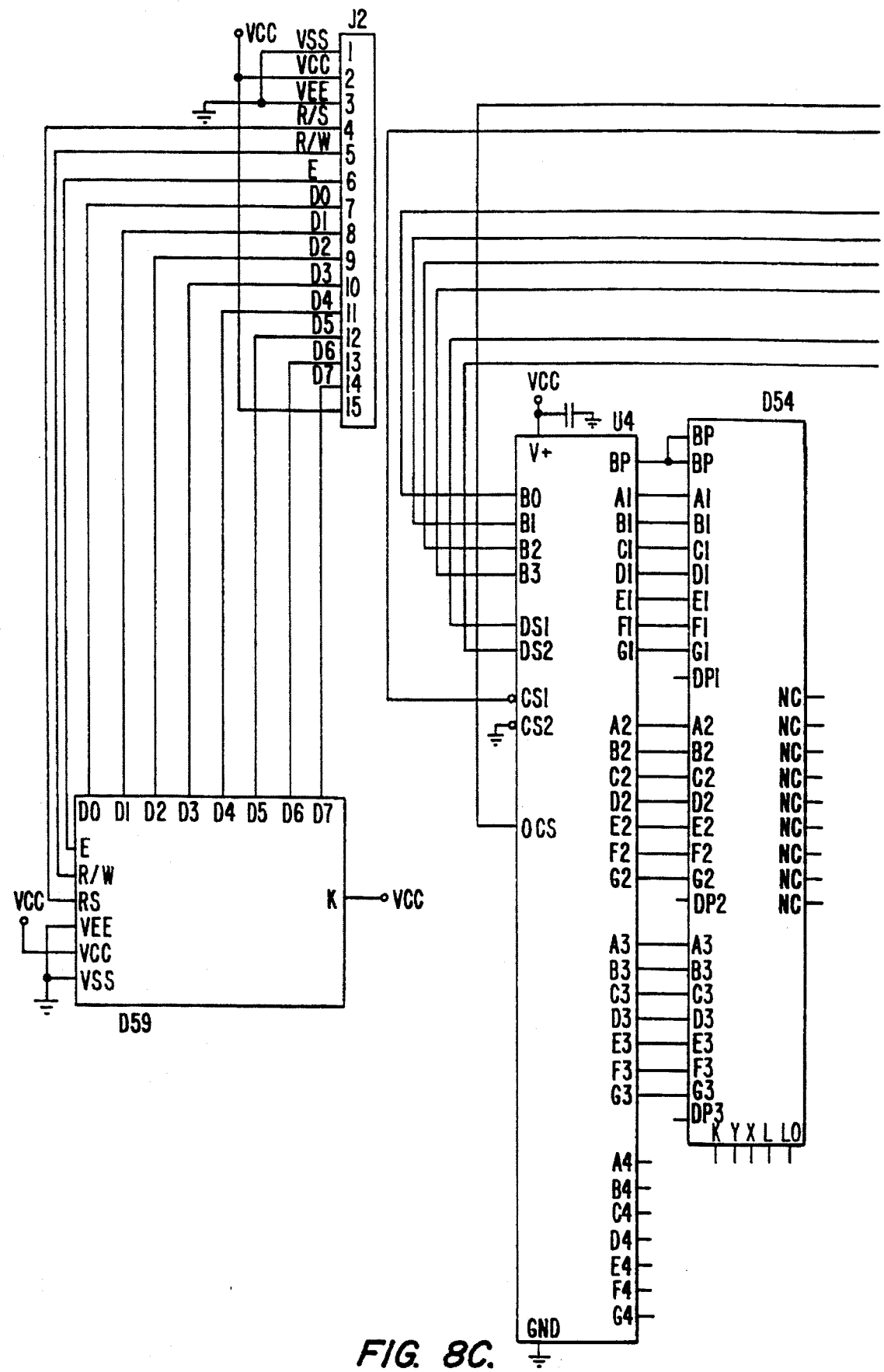
Figure 8D:
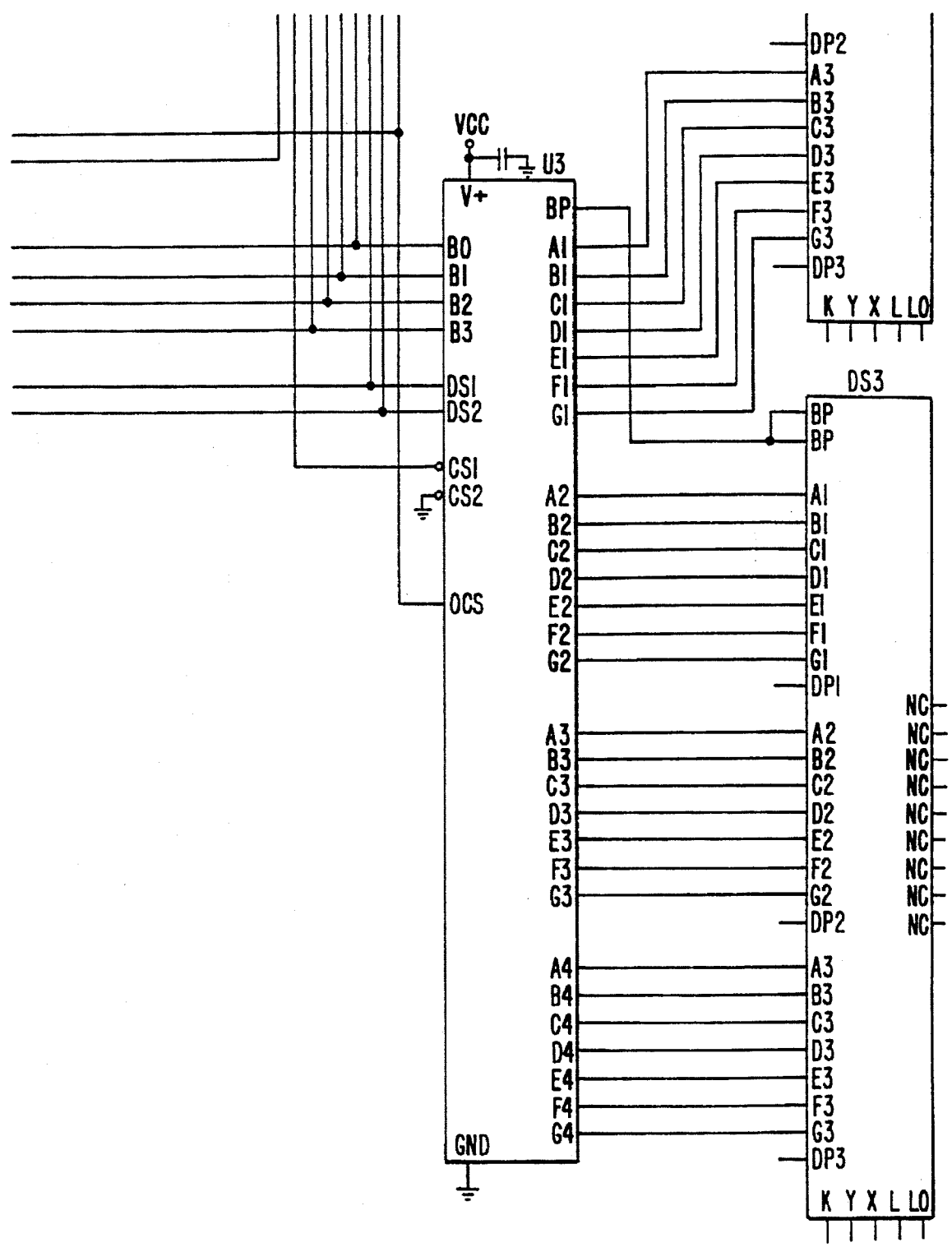
Figure 9A:
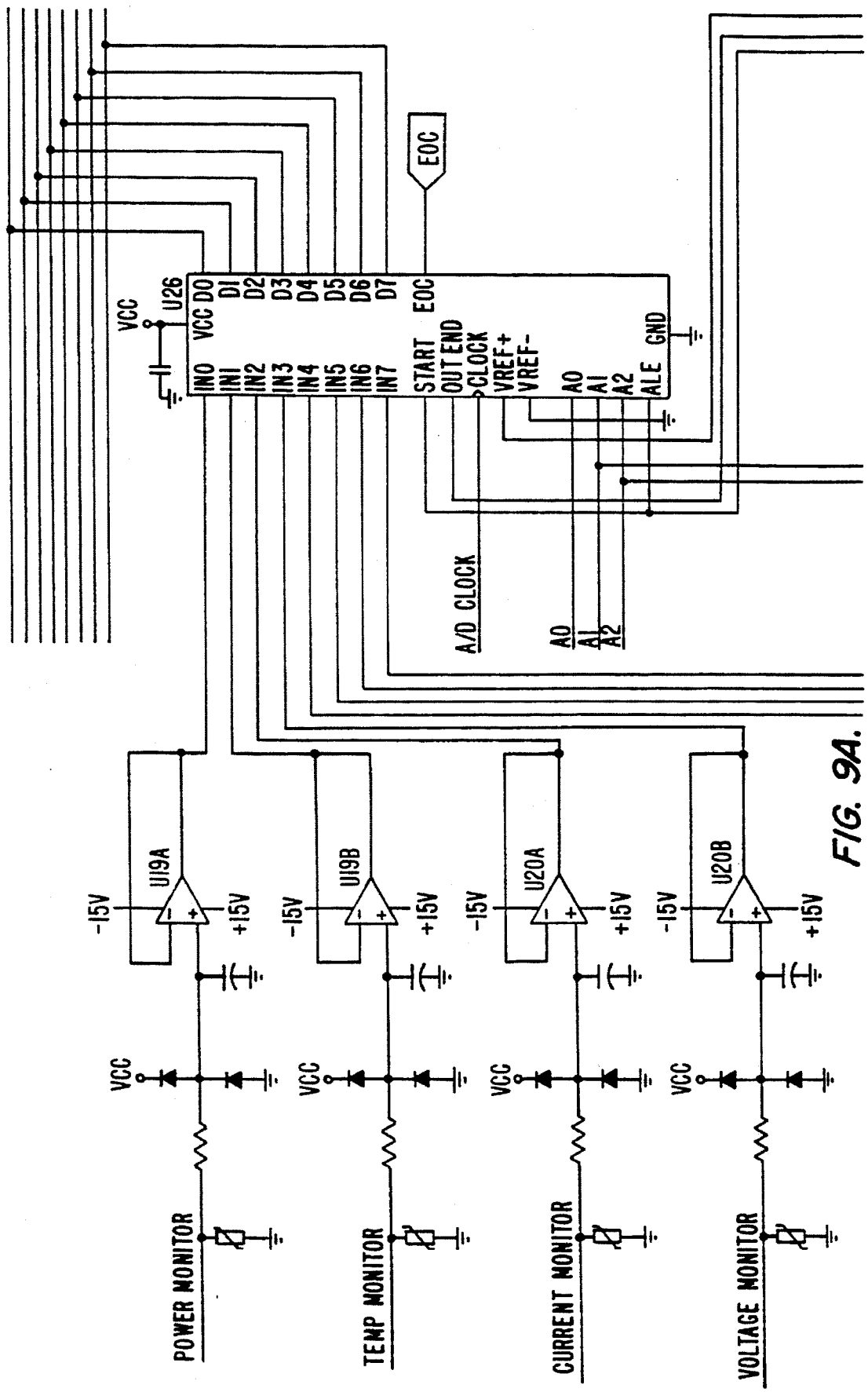
Figure 9B:
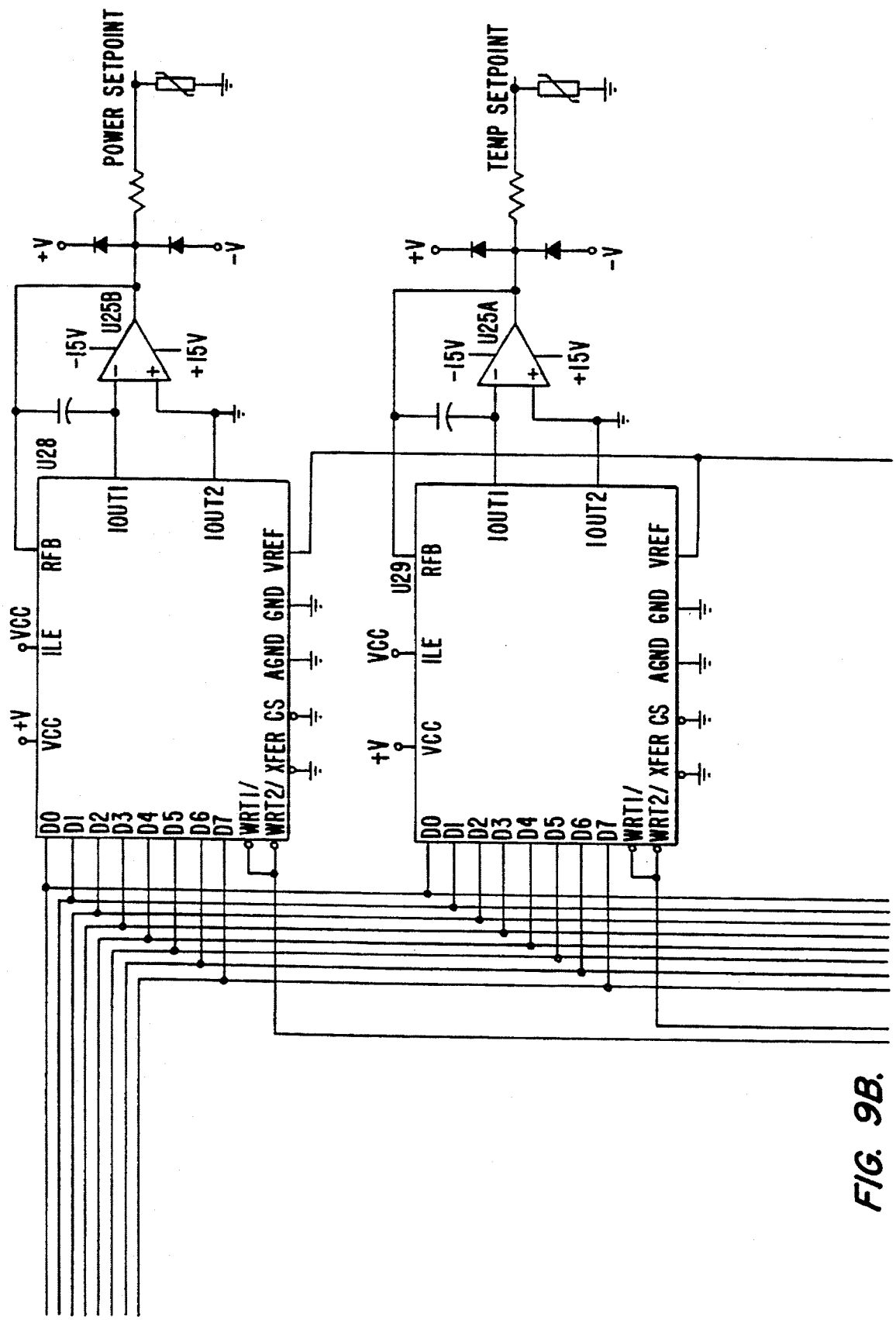
Figure 9D:
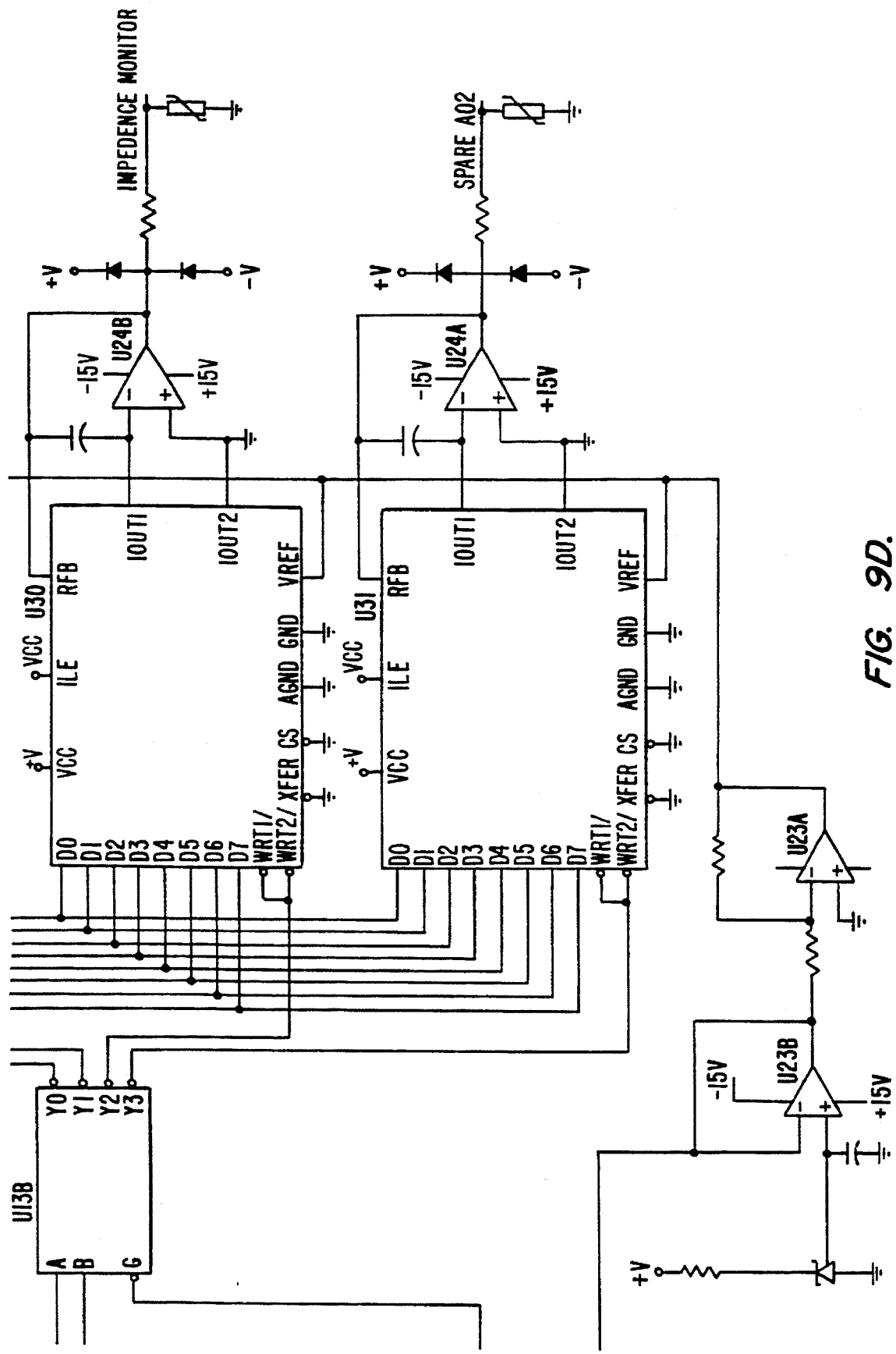
Figures 10, 10D:
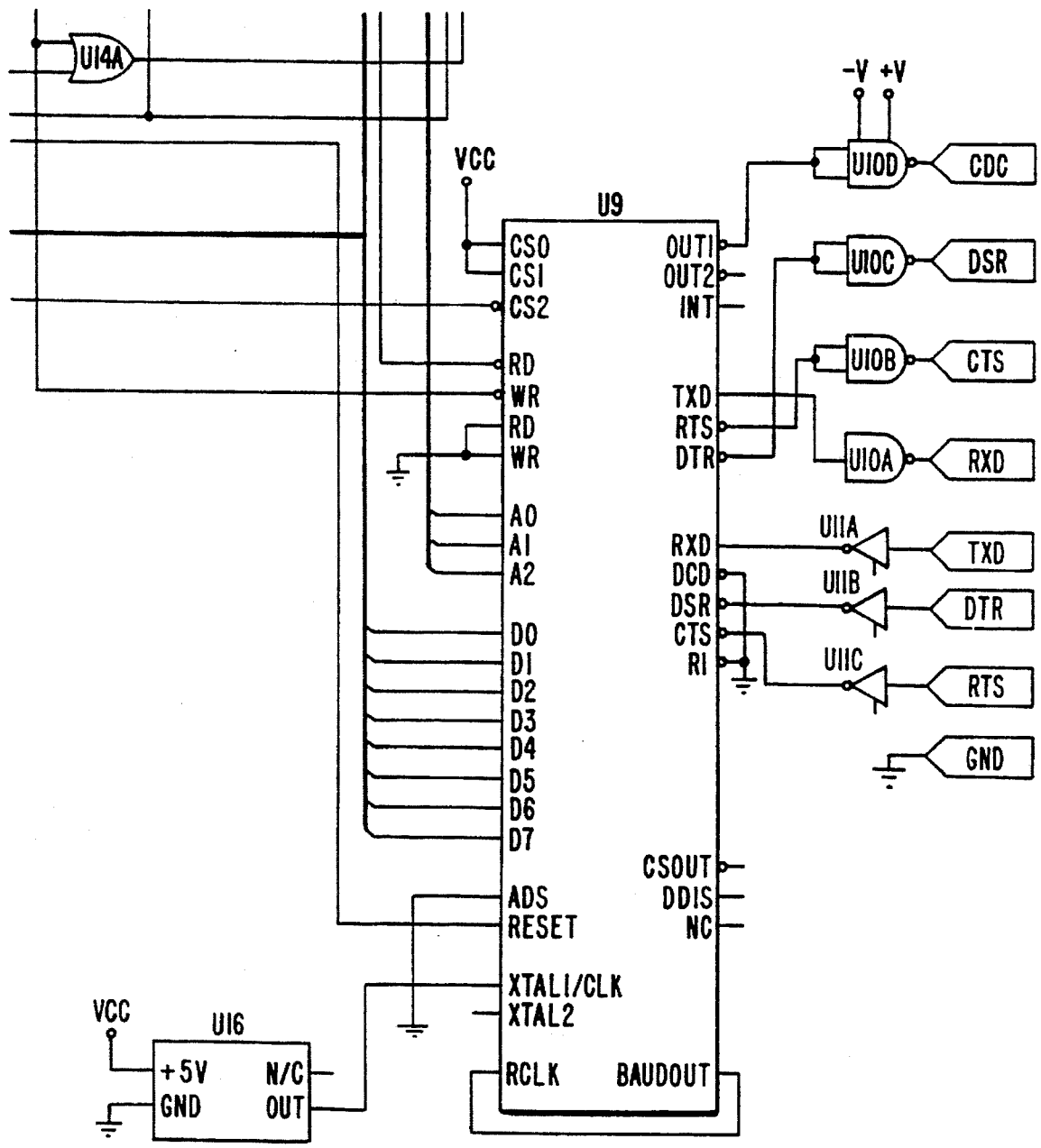
Figure 10A:
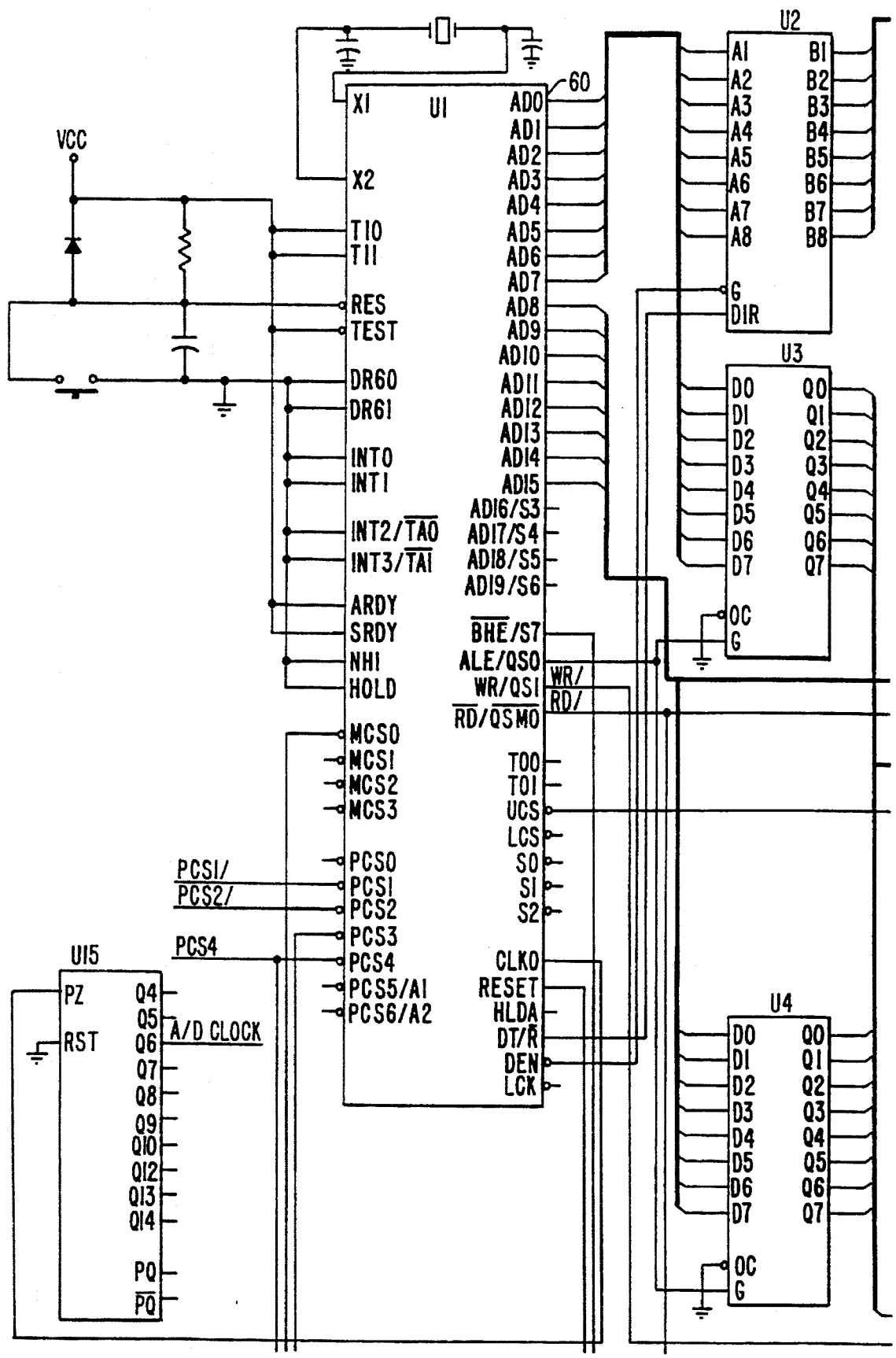
Figure 10B:
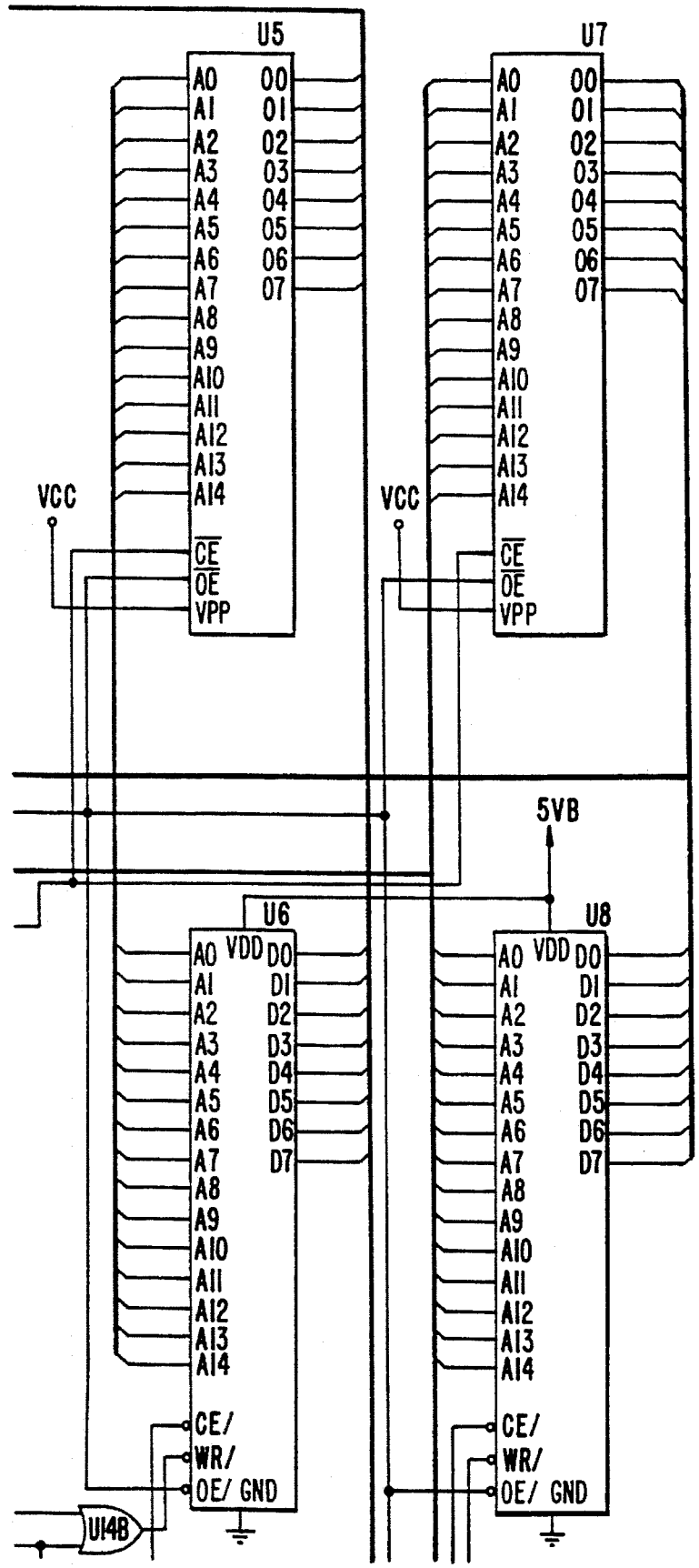
Figure 10C:
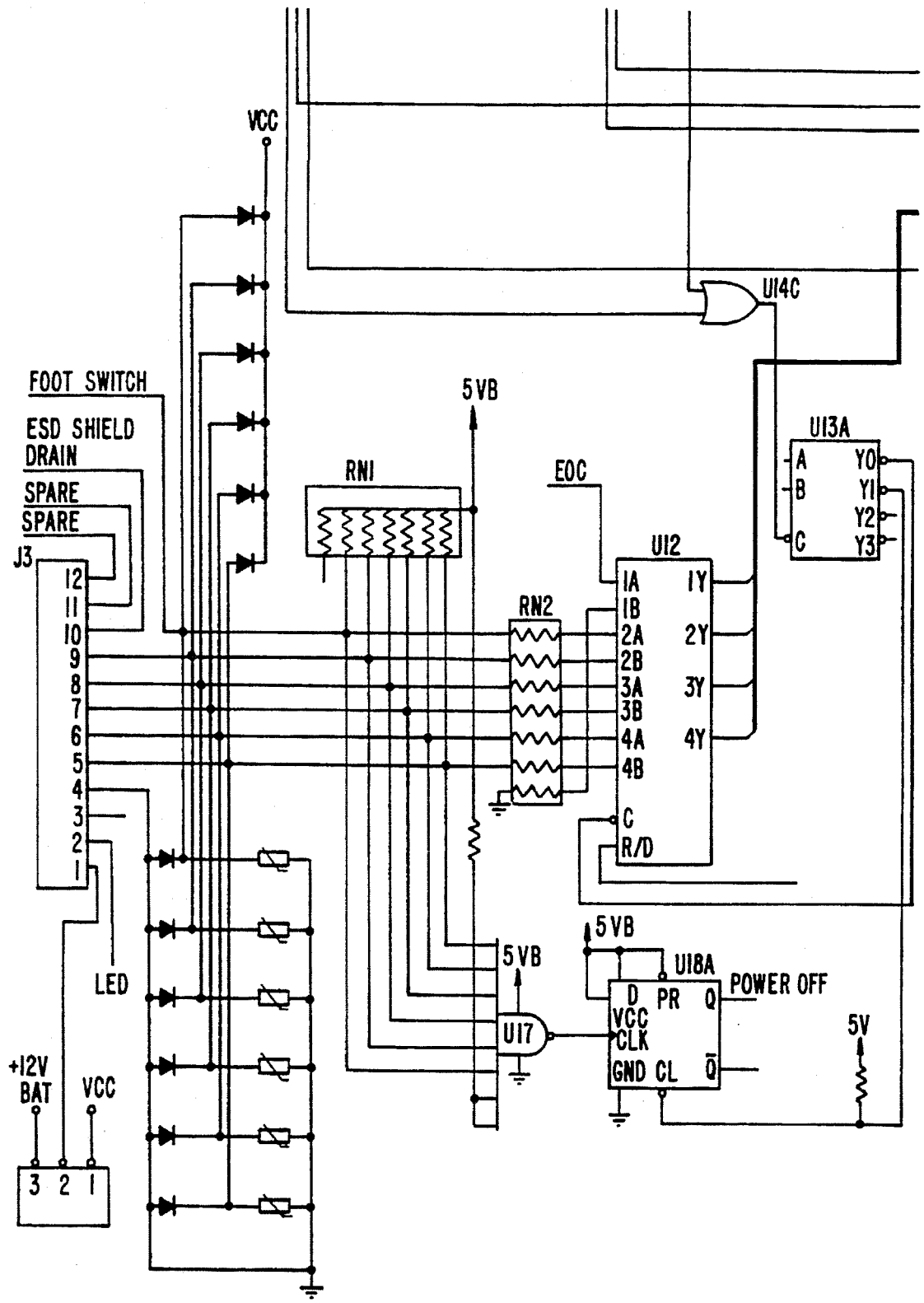
Figure 11C:
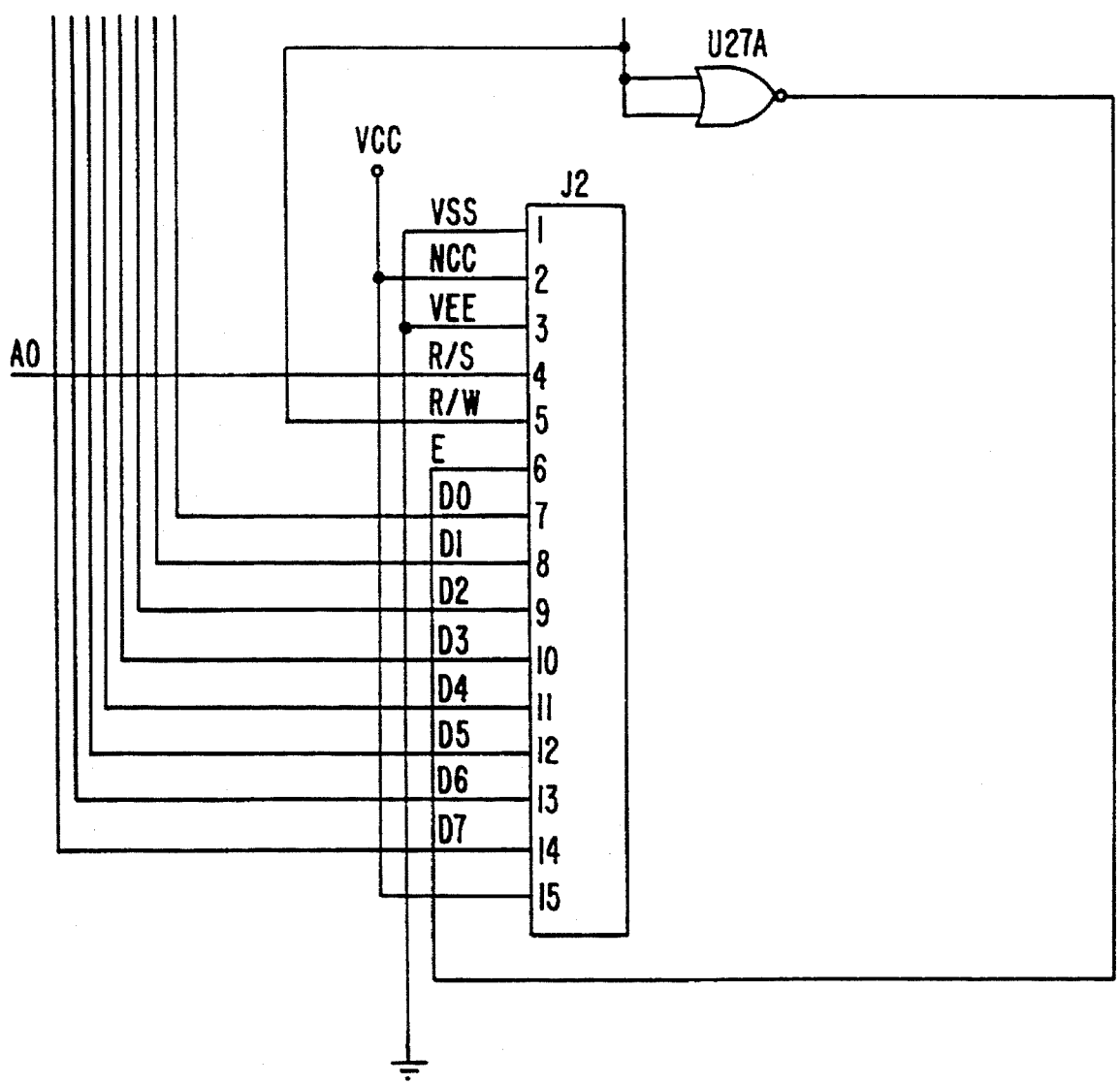
Figure 11:
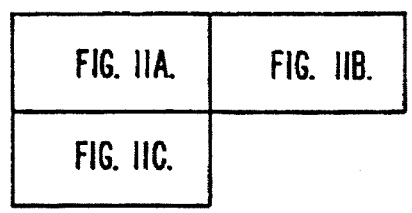
Figure 11A:
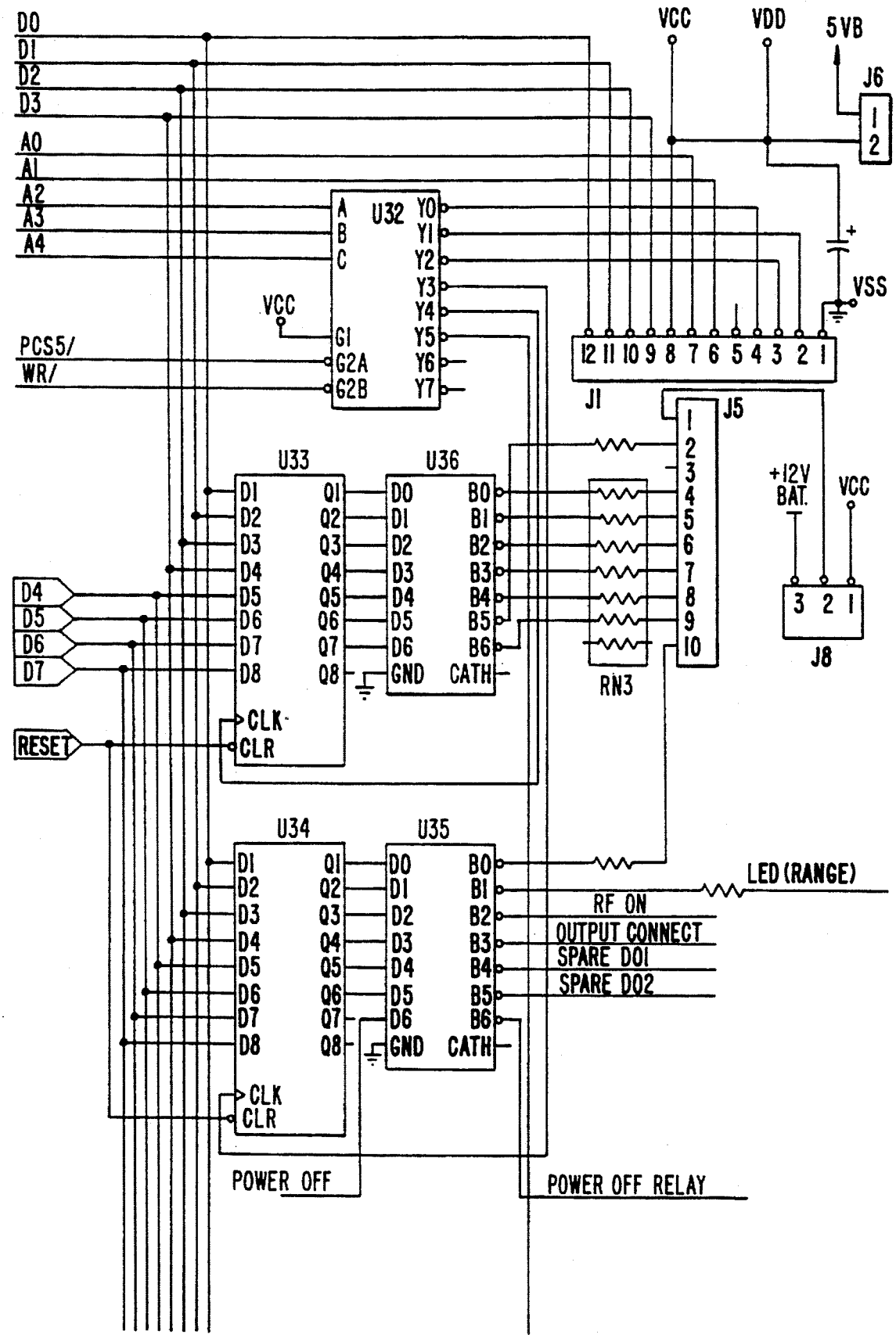
Figure 11B:
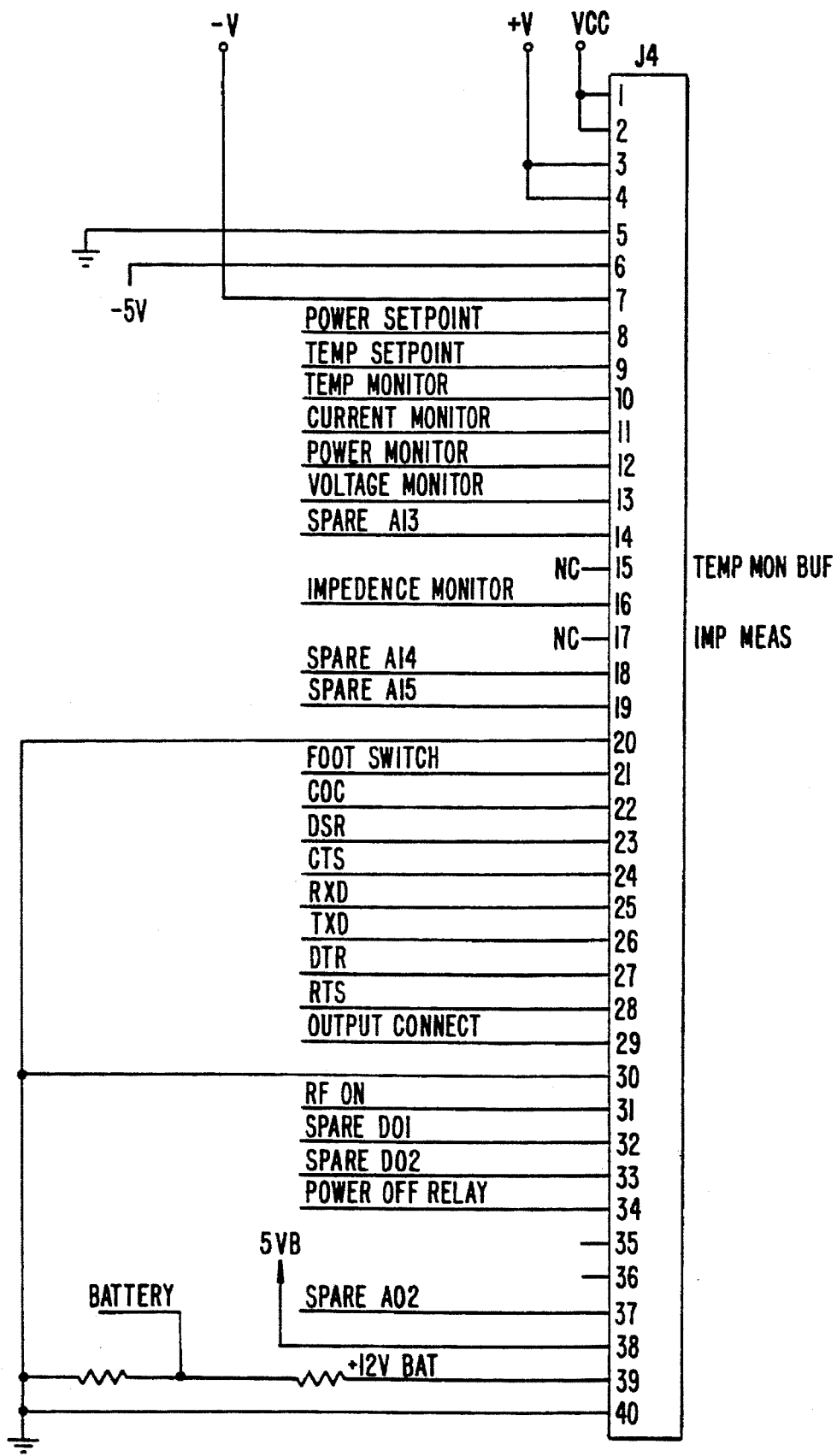

The microprocessor, operating via a 10 MHz clock, constantly monitors all function switches and zeros all DACs (inhibits any RF power command) in the event a malfunction is detected. The RF power generated by the unit cannot exceed 55 W. A comparator 94, shown in FIG. 7, shuts down RF power by limiting the duty cycle to final stage output transformer. Audible and visible alarms are provided in the following conditions: low battery; low/low battery prior to shut-down; low catheter impedance; high/low temperature; high power; and previously used catheter. The low impedance and a previously used catheter conditions inhibit any RF power command. In addition to the software controlled limits for temperature, power, and impedance (that turn off power if exceeded), there are also redundant hardware controls, including comparators 90, 96, that turn off power if the maximum temperature or power is exceeded.

Use of the radiofrequency frequency ablation system 10 will begin by connecting the catheter 12 to the radiofrequency generator 18. After connection, the radiofrequency generator 18 will verify continuity to determine whether the thermocouple or other circuits are intact. This check is performed by delivering a low current signal through lines 22b to the thermocouple 30.

After introducing the catheter to the desired location within the patient's heart, the user will select the desired power delivery mode, i.e. power control or temperature control mode. Of particular interest to the present invention, the temperature control mode utilizes the cascade temperature control scheme described previously. The user selects the desired temperature set point and power is applied with the radiofrequency generator 18 precisely controlling the amount of power delivered in order to maintain the electrode temperature at the set point. Verification of the result of the treatment may be made using the ECG components of the catheter 12, or may be made using other conventional diagnostic techniques. Treatment may be repeated one or more times in order to achieve the desired ablation of the accessory pathway or location on the bundle of HIS.

Although the foregoing invention has been described in some detail by way of illustration and example, for purposes of clarity of understanding, it will be obvious that certain changes and modifications may be practiced within the scope of the appended claims.

What is claimed is:

1. A regulated RF power supply for supplying regulated RF power from the power supply output to automatically raise the temperature of tissue rapidly to a desired temperature and to maintain tissue energized by the RF power at a desired temperature, said power supply comprising:

means for providing a temperature setpoint signal having a magnitude indicating the desired temperature;

means, thermally coupled to the tissue energized by the RF power, for generating an actual temperature signal having a magnitude indicating the actual temperature of the tissue energized by the RF power;

means, coupled to receive said temperature setpoint signal and said actual temperature signal, for generating a power set point signal having a magnitude indicating the difference between the desired temperature and the actual temperature;

means, coupled to the power supply output, for generating an actual power signal having a magnitude indicating the actual real-time magnitude of the regulated RF power supplied by the RF power supply;

means, coupled to receive said power set point signal and said actual power signal, for generating a power output signal having a magnitude indicating the difference between the magnitude of the actual power signal and the power set point signal;

a digital RF signal generator for providing a series of digital values representing a substantially sinusoidal RF signal having a preselected frequency;

a multiplying digital to analog convertor (DAC), having a digital input coupled to said digital RF signal generator, an analog voltage input coupled to receive said power output signal, and an analog output, for providing an analog sinusoidal RF signal at said analog output having said predetermined frequency and having a magnitude controlled by the magnitude of said power output signal to increase the amplitude of the analog RF signal when the actual temperature is much less than the desired temperature to rapidly raise the temperature to the desired temperature and to subsequently reduce the amplitude of the analog RF signal to maintain the desired temperature.

2. The power supply of claim 1 further comprising:

pulsing control means for alternately providing either a power enable signal or power disable signal at selected time intervals; and with said digital RF signal generator coupled to said pulsing control means to receive said power enable and disable signals and further comprising:

pulsing means, responsive to said power enable and disable signal, for providing said RF signal only when said power enable signal is received and providing a null signal otherwise.

3. A system for radiofrequency ablation of cardiac tissue, said system comprising:

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and a radiofrequency power generator connected to said proximal end of the catheter, said generator including:
(a) a power source including a digital RF signal generator for providing a digitized sinusoidal RF signal, a multiplying DAC having a digital input, coupled to receive said digitized RF signal, a reference voltage input for receiving a power output signal having a variable magnitude, and an analog output for delivering, via an amplifier, radiofrequency power to the electrode, based on the magnitude of the power output signal;
(b) means, coupled to said power source, for measuring radiofrequency power delivered from the power source to the electrode to produce an actual power signal;
(c) an analog temperature controller which receives a temperature set point signal and an actual temperature signal from the temperature sensor and based on a difference therebetween produces a power set point signal;
(d) an analog power controller coupled the means for measuring radiofrequency power and to the analog temperature controller where the analog power controller receives the power set point signal and the actual power signal and based on a difference therebetween varies the magnitude the power output signal;
(e) control means, coupled to said analog temperature controller, for providing said temperature set point signal; and
(f) means for connecting said power source to said electrode connection wire and for connecting said temperature controller to said temperature sensor connection wire.

4. The power supply of claim 2 further comprising:

pulsing control means for alternately providing either a power enable signal or power disable signal at selected time intervals; and with said digital RF signal generator coupled to said pulsing control means to receive said power enable and disable signals and further comprising:

pulsing means, responsive to said power enable and disable signal, for providing said RF signal only when said power enable signal is received and providing a null signal otherwise.

5. A system for radiofrequency ablation of tissue, said system comprising:

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and a radiofrequency power generator connectable to the proximal end of the catheter, said generator including:
(a) power supply means for delivering radiofrequency power to the electrode based on a power output signal;
(b) means for controlling temperature at the temperature sensor, said means being connected to receive an actual temperature signal from the sensor and to modulate the power output signal to have an amplitude proportional to the difference between said actual temperature signal and a temperature set point; and
(c) a battery connected to said power supply means and said means for controlling as the sole source of power for said radiofrequency power generator to reduce or eliminate spurious ground differential currents;
(d) means for connecting said power supply means to said electrode connection wire and for connecting said temperature control means to said temperature sensor connection wire.

6. A system as in claim 5, wherein the electrode is at the distal tip of the catheter.

7. A system as in claim 5, wherein the power supply means comprises a radiofrequency oscillator coupled to a power transformer.

8. A system as in claim 7, wherein the power transformer is coupled to the power controller to receive said power output signal.

9. A system as in claim 5 further comprising means for optically isolating the temperature sensor from the radiofrequency power generator.

10. A system for radiofrequency ablation, said system comprising:

a catheter having a proximal end, a distal end, an electrode near the distal end, a thermocouple near the distal end for measuring temperature near the distal end, and a verification circuit near the proximal end for testing the electrical continuity of the thermocouple, said electrode being coupled to an electrode connection wire extending to the proximal end;

a radiofrequency power generator connectable to the proximal end of the catheter;

means, coupled to said thermocouple, for providing a high/low temperature warning when the temperature near the distal end is outside a selected range;

a current source for supplying a current to the verification circuit when the electrical continuity of the of the thermocouple is to be tested;

means for sensing current flow through the verification circuit;

means for connecting the radiofrequency power generator to the electrode connector wire and for connecting the current source to the verification circuit; and means for disabling the radiofrequency power generator when the current flow through the verification circuit is outside a selected range.

11. A system as in claim 10 wherein the sensing means comprises a microprocessor coupled to a voltage sensor responsive to the voltage across the verification circuit.

12. A system as in claim 10 wherein the means for disabling comprises a relay coupled to a microprocessor and coupled to the connecting means.

13. A system as in claim 10 wherein the verification circuit comprises a short circuit when the current flow through the verification circuit is within the selected range.

14. A system for radiofrequency ablation of tissue, said system comprising:
  a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and
  a radiofrequency power generator connectable to the proximal end of the catheter, said generator including:
    (a) a power source which delivers radiofrequency power to the electrode based on a power output signal and provides an actual power signal indicating the magnitude of the radiofrequency power delivered;
    (b) means for controlling temperature at the temperature sensor, said means being connected to receive an actual temperature signal from the sensor, said actual power signal, and to modulate the power output signal based on a said actual power signal and a control signal having a magnitude indicating the difference between said actual temperature signal and a temperature set point;
    (c) means for connecting said power source to said electrode connection wire and for connecting said temperature control means to said temperature sensor connection wire; and
    (d) means for providing an alternative control signal having a magnitude indicating a selected power level;
    (e) means, coupled to said means for providing said alternative control signal and to receive said actual power signal, for limiting the radiofrequency power delivered to said electrode according to the magnitude of said alternative control signal and said actual power signal and irrespective of said actual temperature signal or said temperature set point.

15. A system as in claim 14 wherein said limiting means comprises a comparator coupled to said radiofrequency power source and to said connecting means.

16. A system as in claim 14 further comprising first means for disabling operation of said radiofrequency power generator based on a first parameter selected from the group including impedance of said electrode, radiofrequency power delivered to said electrode, and said actual temperature signal.

17. A system as in claim 16 wherein said first disabling means comprises a microprocessor coupled to said power source, said microprocessor controlled by a software program programmed to disable said radiofrequency power generator if at least one of said first parameters exceeds a first limit.

* * * * *